United States Patent
Kim et al.

(10) Patent No.: US 10,696,725 B2
(45) Date of Patent: Jun. 30, 2020

(54) GLUCAGON DERIVATIVE AND A COMPOSITION COMPRISING A LONG ACTING CONJUGATE OF THE SAME

(71) Applicant: HANMI PHARM. CO., LTD., Hwaseong-si, Gyeonggi-do (KR)

(72) Inventors: Jung Kuk Kim, Hwaseong-si (KR); Young Jin Park, Hwaseong-si (KR); In Young Choi, Hwaseong-si (KR); Sung Youb Jung, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 15/740,668

(22) PCT Filed: Jun. 29, 2016

(86) PCT No.: PCT/KR2016/006984
§ 371 (c)(1),
(2) Date: Dec. 28, 2017

(87) PCT Pub. No.: WO2017/003191
PCT Pub. Date: Jan. 5, 2017

(65) Prior Publication Data
US 2018/0186853 A1   Jul. 5, 2018

(30) Foreign Application Priority Data
Jun. 30, 2015   (KR) .................. 10-2015-0093265

(51) Int. Cl.
| | | |
|---|---|---|
| A61K 38/26 | (2006.01) | |
| A61K 38/28 | (2006.01) | |
| C07K 14/605 | (2006.01) | |
| A61K 38/22 | (2006.01) | |
| A61K 47/60 | (2017.01) | |
| A61K 47/68 | (2017.01) | |
| A61P 3/08 | (2006.01) | |
| A61P 3/00 | (2006.01) | |
| A61P 3/04 | (2006.01) | |

(52) U.S. Cl.
CPC ........ *C07K 14/605* (2013.01); *A61K 38/2264* (2013.01); *A61K 38/2278* (2013.01); *A61K 38/26* (2013.01); *A61K 38/28* (2013.01); *A61K 47/60* (2017.08); *A61K 47/68* (2017.08); *A61K 47/6811* (2017.08); *A61P 3/00* (2018.01); *A61P 3/04* (2018.01); *A61P 3/08* (2018.01)

(58) Field of Classification Search
None
See application file for complete search history.

(56) References Cited

U.S. PATENT DOCUMENTS

| | | | |
|---|---|---|---|
| 5,408,037 | A | 4/1995 | Smith et al. |
| 7,994,122 | B2 | 8/2011 | Riber et al. |
| 8,450,270 | B2 | 5/2013 | Dimarchi et al. |
| 8,454,971 | B2 | 6/2013 | Day et al. |
| 8,507,428 | B2 | 8/2013 | DiMarchi et al. |
| 8,703,701 | B2 | 4/2014 | Dimarchi |
| 2006/0275254 | A1* | 12/2006 | Kim ...................... C07K 19/00 424/85.1 |
| 2009/0111739 | A1 | 4/2009 | Kajihara et al. |
| 2010/0105877 | A1 | 5/2010 | Song et al. |
| 2010/0190699 | A1 | 7/2010 | DiMarchi et al. |
| 2010/0190701 | A1 | 7/2010 | Day et al. |
| 2010/0330108 | A1* | 12/2010 | Song ...................... C07K 19/00 424/179.1 |
| 2011/0082079 | A1 | 4/2011 | Spetzler et al. |
| 2012/0165503 | A1 | 6/2012 | Carrington et al. |
| 2012/0288511 | A1 | 11/2012 | Dimarchi |
| 2012/0329715 | A1 | 12/2012 | Greig et al. |
| 2013/0116173 | A1 | 5/2013 | Dimarchi et al. |
| 2013/0143798 | A1* | 6/2013 | Lau ...................... C07K 14/605 514/5.3 |
| 2013/0203659 | A1 | 8/2013 | Miranda et al. |
| 2014/0011738 | A1 | 1/2014 | DiMarchi |
| 2014/0128318 | A1* | 5/2014 | Jung .................... C07K 14/605 514/4.8 |
| 2015/0164997 | A1 | 6/2015 | Haack et al. |
| 2015/0368310 | A1 | 12/2015 | Dimarchi et al. |
| 2018/0311315 | A1 | 11/2018 | Oh et al. |

FOREIGN PATENT DOCUMENTS

| | | | |
|---|---|---|---|
| EA | 201791333 | A1 | 12/2017 |
| JP | 5476304 | B2 | 2/2014 |
| JP | 2014-507402 | A | 3/2014 |
| JP | 2015-521622 | A | 7/2015 |
| KR | 10-2009-0096498 | A | 9/2009 |
| KR | 10-2012-0010146 | A | 2/2012 |
| KR | 10-2012-0052973 | A | 5/2012 |

(Continued)

OTHER PUBLICATIONS

BioSynthesis, "N-Terminal Acetylation Amidation Peptides Chemically Synthesized Aminopeptidases Intracellular", Nov. 11, 2008, 1 page, accessed at URL biosyn.com/faq/why-acetylate-and-amidate-a-peptide.aspx (Year: 2008).*
Cornier, "The metabolic syndrome," Endocrine Rev. 29:777-822 (2008) (Year: 2008).*
United States Patent and Trademark; Communication dated May 2, 2019, issued in U.S. Appl. No. 15/540,729.
"The Isoelectric Point", Chapter 23.4, Chemistry LibreTexts, Jul. 29, 2014 (13 pages total).
Perfetti, et al., "Glucagon-like peptide-1: a major regulator of pancreatic β-cell function", European Journal of Endocrinology, 2000, vol. 143, pp. 717-725 (9 pages total).
Gutniak, et al., "Antidiabetogenic Effect of Glucagon-Like Peptide-I (7-36)Amide in Normal Subjects and Patients With Diabetes Mellitus", The New England Journal of Medicine, May 14, 1992, pp. 1316-1322 (7 pages total).
Australian Patent Office; Communication dated Jul. 31, 2018 in Australian application No. 2016382393.
Australian Patent Office; Communication dated Jul. 31, 2018 in Australian application No. 2016382394.

(Continued)

*Primary Examiner* — Julie Ha
*Assistant Examiner* — Kristina M Hellman
(74) *Attorney, Agent, or Firm* — Sughrue Mion, PLLC

(57) ABSTRACT

The present invention relates to a glucagon derivative, a long-acting conjugate of the glucagon derivative, and a use thereof.

27 Claims, 5 Drawing Sheets
Specification includes a Sequence Listing.

(56) References Cited

FOREIGN PATENT DOCUMENTS

| | | |
|---|---|---|
| KR | 10-2013-0018410 A | 2/2013 |
| KR | 10-2014-0018462 A | 2/2014 |
| KR | 101382593 B1 | 4/2014 |
| KR | 10-2015-0096398 A | 8/2015 |
| KR | 10-2015-0096433 A | 8/2015 |
| MA | 40709 A1 | 12/2017 |
| MA | 41887 A1 | 12/2018 |
| TW | 201307380 A1 | 2/2013 |
| WO | 96/16196 A2 | 5/1996 |
| WO | 96/16196 A3 | 5/1996 |
| WO | 96/32478 A1 | 10/1996 |
| WO | 97/34631 A1 | 9/1997 |
| WO | 0183527 A2 | 11/2001 |
| WO | 2004/093823 A2 | 11/2004 |
| WO | 2008101017 A2 | 8/2008 |
| WO | 2009099763 A1 | 8/2009 |
| WO | 2010/011439 A2 | 1/2010 |
| WO | 2010/096052 A1 | 8/2010 |
| WO | 2010148089 A1 | 12/2010 |
| WO | 2011038900 A2 | 4/2011 |
| WO | 2011/075393 A2 | 6/2011 |
| WO | 2011/088837 A1 | 7/2011 |
| WO | 2011/117415 A1 | 9/2011 |
| WO | 2011143208 A1 | 11/2011 |
| WO | 2012/011752 A2 | 1/2012 |
| WO | 2012/088116 A2 | 6/2012 |
| WO | 2012/158965 A2 | 11/2012 |
| WO | 2012150503 A2 | 11/2012 |
| WO | 2012/173422 A1 | 12/2012 |
| WO | 2012169798 A2 | 12/2012 |
| WO | 2013/004983 A1 | 1/2013 |
| WO | 2013/074910 A1 | 5/2013 |
| WO | 2013/192129 A1 | 12/2013 |
| WO | 2013/192130 A1 | 12/2013 |
| WO | 2014/017843 A1 | 1/2014 |
| WO | 2014049610 A2 | 4/2014 |
| WO | 2014/073842 A1 | 5/2014 |
| WO | 2014/073845 A1 | 5/2014 |
| WO | 2014/081864 A1 | 5/2014 |
| WO | 2014/081872 A1 | 5/2014 |
| WO | 2014/096145 A1 | 6/2014 |
| WO | 2014/096150 A1 | 6/2014 |
| WO | 2014/170496 A1 | 10/2014 |
| WO | 2015/183054 A1 | 12/2015 |
| WO | 2016/043533 A1 | 3/2016 |
| WO | 2016/049190 A1 | 3/2016 |
| WO | 2016/108586 A1 | 7/2016 |
| WO | 2017/003191 A1 | 1/2017 |

OTHER PUBLICATIONS

Brian Finan, et al., "A rationally designed monomeric peptide triagonist corrects obesity and diabetes in rodents", Nat Med., Jan. 2015, 1-13 pages, vol. 21, No. 1.

Daniel J. Drucker, et al., "The Incretin system: glucagon-like peptide-1 receptor agonists and dipeptidyl peptidase-4 inhibitors in type 2 diabetes", The Lancet, 2006, pp. 1696-1705, vol. 368, No. 11.

International Searching Authority; International Search Report for PCT/KR2016/015554 dated Apr. 10, 2017 [PCT/ISA/210].

International Searching Authority; International Search Report for PCT/KR2016/015555 dated Apr. 10, 2017 [PCT/ISA/210].

Jonathan W. Day, et al., "A new glucagon and GLP-1 co-agonist eliminates obesity in rodents", Nature Chemical Biology, Oct. 2009, pp. 749-757, vol. 5, No. 10.

Korean Intellectual Property Office, Communication dated Jul. 11, 2018, issued in Korean Application No. 10-2016-0183499, No translation.

Korean Intellectual Property Office, Communication dated Jul. 11, 2018, issued in Korean Application No. 10-2016-0183500, No translation.

Yahiya Y. Syed, et al., "Exenatide Extended-Release: An Updated Review of Its Use in Type 2 Diabetes Mellitus", Drugs, Jun. 2015, 12 pages, vol. 10.

"Calculating approximate isoelectric points for amino acids and peptides", Nov. 1, 2011, pp. 1-2, XP055471990, Retrieved from the Internet: URL:http://www.elcamino.edu/faculty/pdoucette/calculating-approximate-isoelectric-points.pdf (2 pages total).

Colombia Patent Office; Communication dated Jul. 17, 2018 in Colombian application No. NC2017/0006308, No translation.

European Patent Office; Communication dated Jun. 12, 2018 in European application No. 15875680.9.

United States Patent and Trademark Office; Communication dated Oct. 31, 2018, issued in U.S. Appl. No. 16/024,014.

International Searching Authority; International Search Report for PCT/KR2015/014422 dated Apr. 14, 2016 (PCT/ISA/210), English translation.

Joseph Chabenne et al., "A glucagon analog chemically stabilized for immediate treatment of life-threatening hypoglycemia," Molecular Metabolism, Jan. 2014, pp. 293-300, vol. 3.

Kevin L. Shaw et al., "The effect of net charge on the solubility, activity, and stability of ribonuclease Sa," Protein Science, 2001, pp. 1206-1215, vol. 10 (11 pages total).

Australian Patent Office; Communication dated Feb. 7, 2019 in Australian application No. 2017289014.

Cecilia G. Unson et al., "The Role of Histidine-1 in Glucagon Action", Archives of Biochemistry and Biophysics, vol. 300, No. 2, Feb. 1, 1993, pp. 747-750 (6 pages total), CAplus accession No. DN 118:205395.

Ecuador Patent Office; Communication dated Feb. 3, 2018 in Ecuadorian application No. IEPI-2018-3879, No translation.

Ecuador Patent Office; Communication dated Feb. 3, 2019 in Ecuadorian application No. SENADI-2018-53053, No translation.

Ecuador Patent Office; Communication dated Feb. 3, 2019 in Ecuadorian application No. SENADI-2018-53055, No translation.

International Searching Authority; International Search Report for PCT/KR2017/006922 dated Dec. 7, 2017 (PCT/ISA/210).

United States Patent and Trademark Office; Communication dated Feb. 27, 2019, issued in U.S. Appl. No. 16/023,994.

United States Patent and Trademark Office; Communication dated Jan. 11, 2019, issued in U.S. Appl. No. 16/024,014.

Korean Intellectual Property Office; Communication dated Jul. 12, 2018 in counterpart application No. 10-2016-0081976, Concise Explanation.

Korean Application No. 10-2015-0093265 filed on Jun. 30, 2015 with Translation (total 92 pages).

United States Patent and Trademark Office; Communication dated Jul. 8, 2019, issued in U.S. Appl. No. 16/233,890.

"Endocrine Abstracts", 43rd Annual Meeting of the British Society for Paediatric Endocrinology and Diabetes 2015, Nov. 2015, vol. 39, (total 77 pages).

Eng et al., "Isolation and Characterization of Exendin-4, an Exendin-3 Analogue, from Heloderma suspectum Venom," The Journal of Biological Chemistry, Apr. 15, 1992, vol. pp. 7402-7405, vol. 267, No. 11, Cited and discussed in the specification beginning on p. 2.

Gasteiger et al., "ExPASy: the proteomics server for in-depth protein knowledge and analysis," Nucleic Acids Research, 2003, pp. 3784-3788. vol. 31, No. 13, 2003.

International Search Report for PCT/KR2016/006984, dated Sep. 12, 2016 (PSA/ISA/210).

Written Opinion of the International Searching Authority for PCT/KR2016/006984, dated Sep. 12, 2017 (PCT/ISA/237).

Santoprete et al., "DPP-IV-resistant, long-acting oxyntomodulin derivatives", Journal of Peptide Science, vol. 17, No. 4, Apr. 1, 2011, pp. 270-280, XP055000397.

Unson et al., "The Role of Histidine-1 in Glucagon Action", Archives of Biochemistry And Biophysics, Feb. 1, 1993, vol. 300, No. 2, pp. 747-750 (total 5 pages).

Krstenansky et al., "Examination of the Conformational Requirements Glucagon at its Receptor", Peptides Structure and Function, Proceedings of the Ninth American Peptide Symposium, 1985. pp. 591-594 (total 8 pages).

* cited by examiner

[Figure 1]
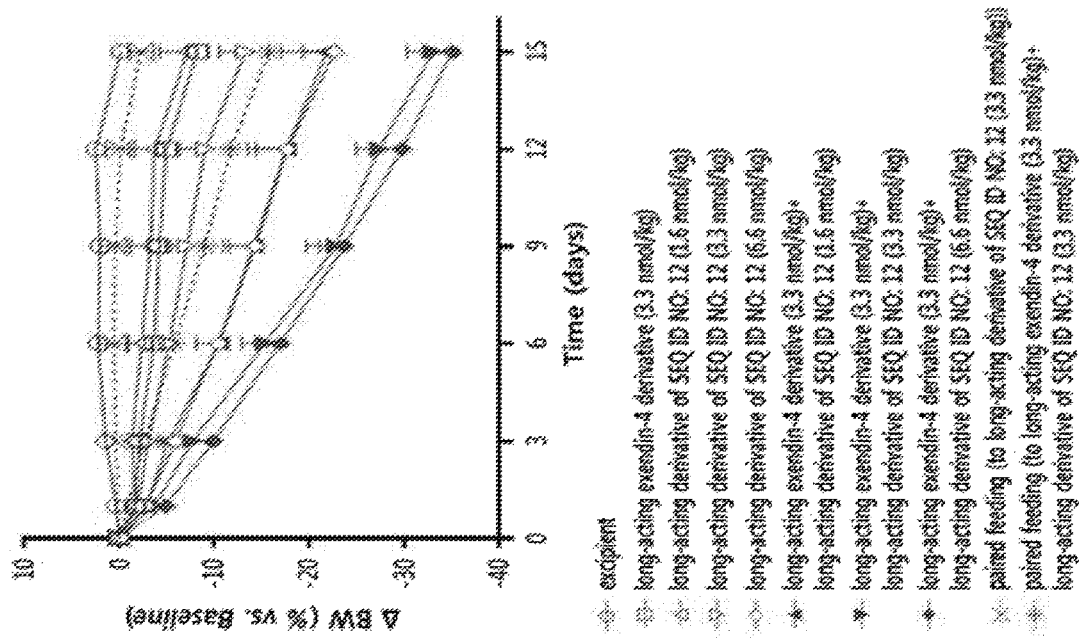

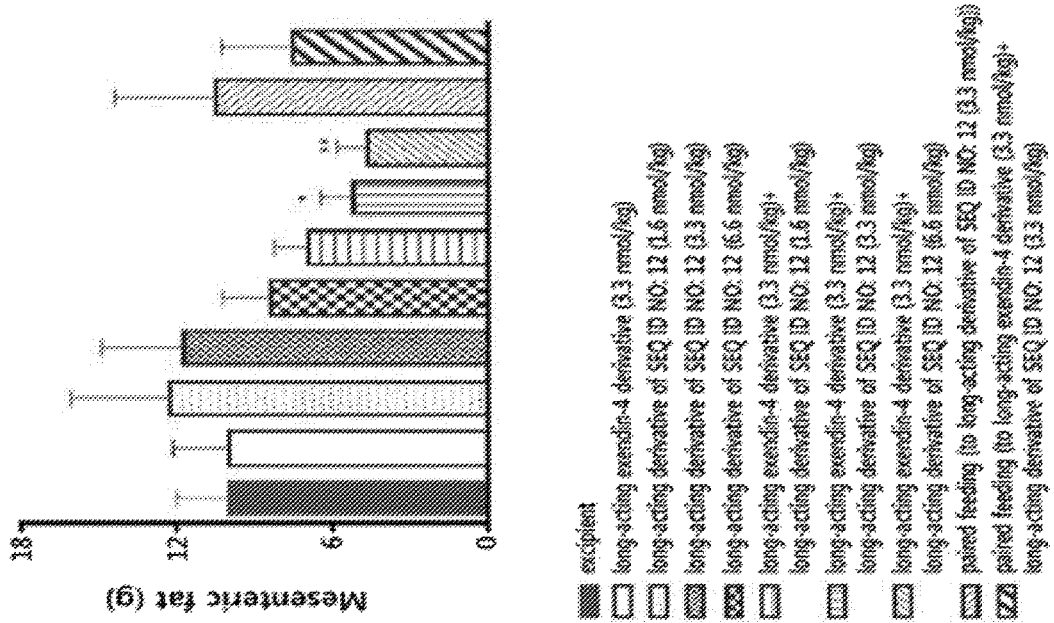
[Figure 2]

[Figure 3]
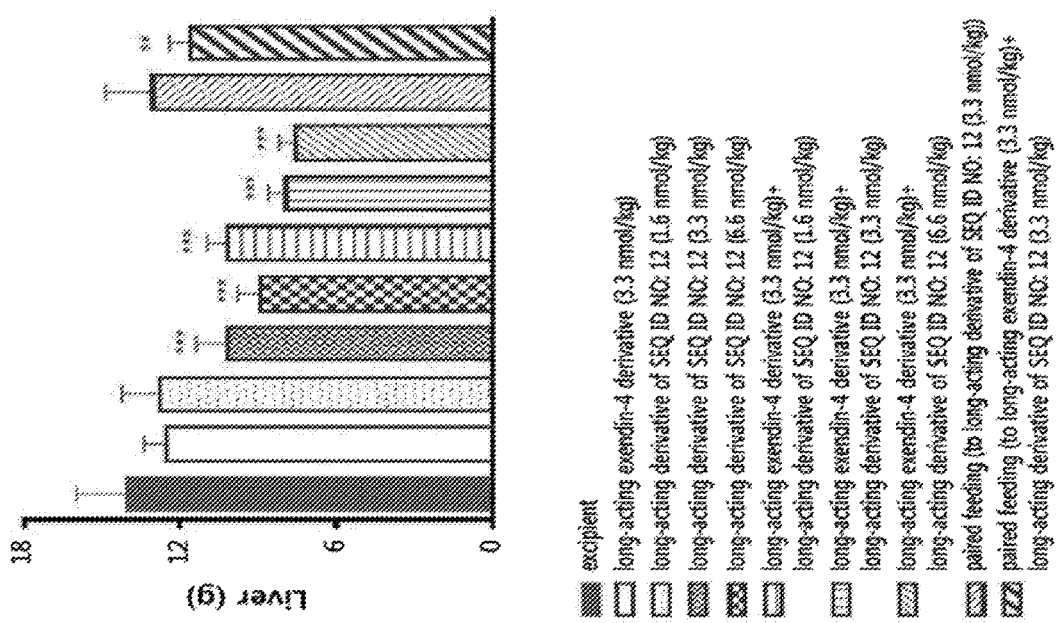

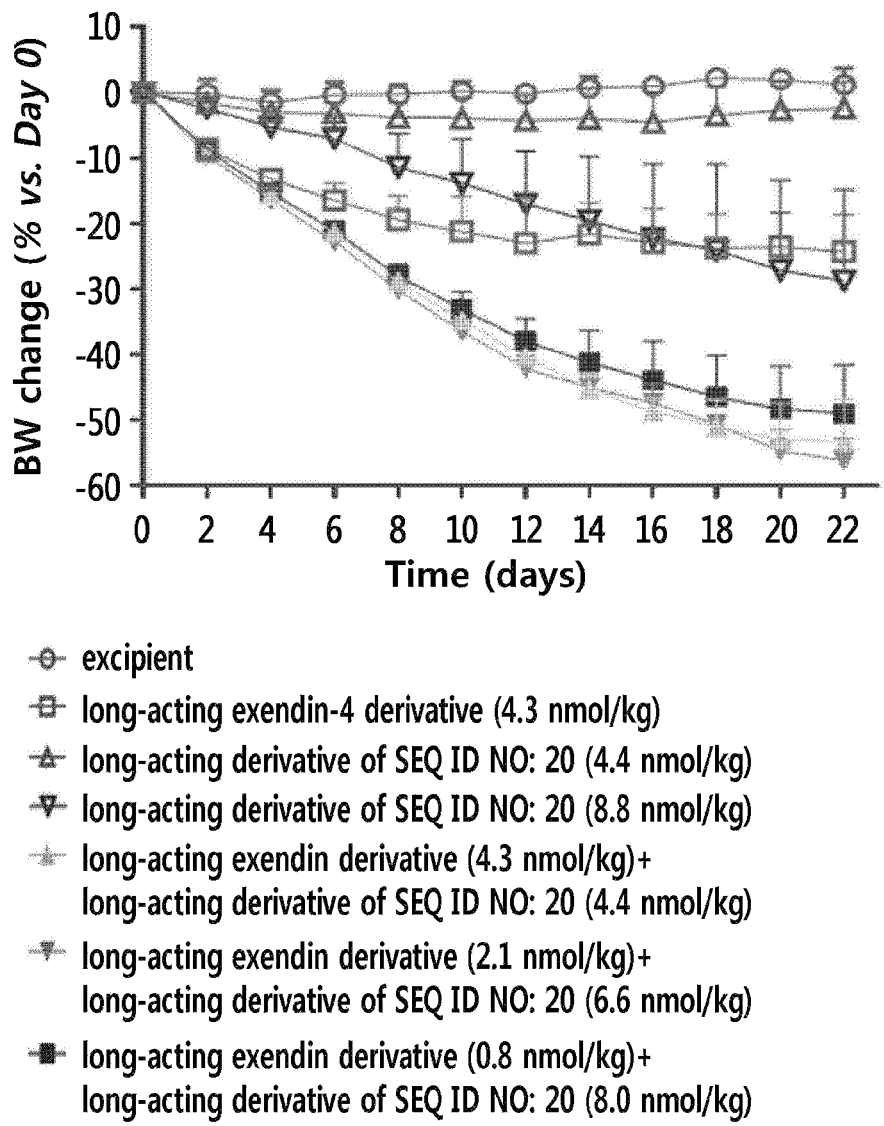
[Figure 4]

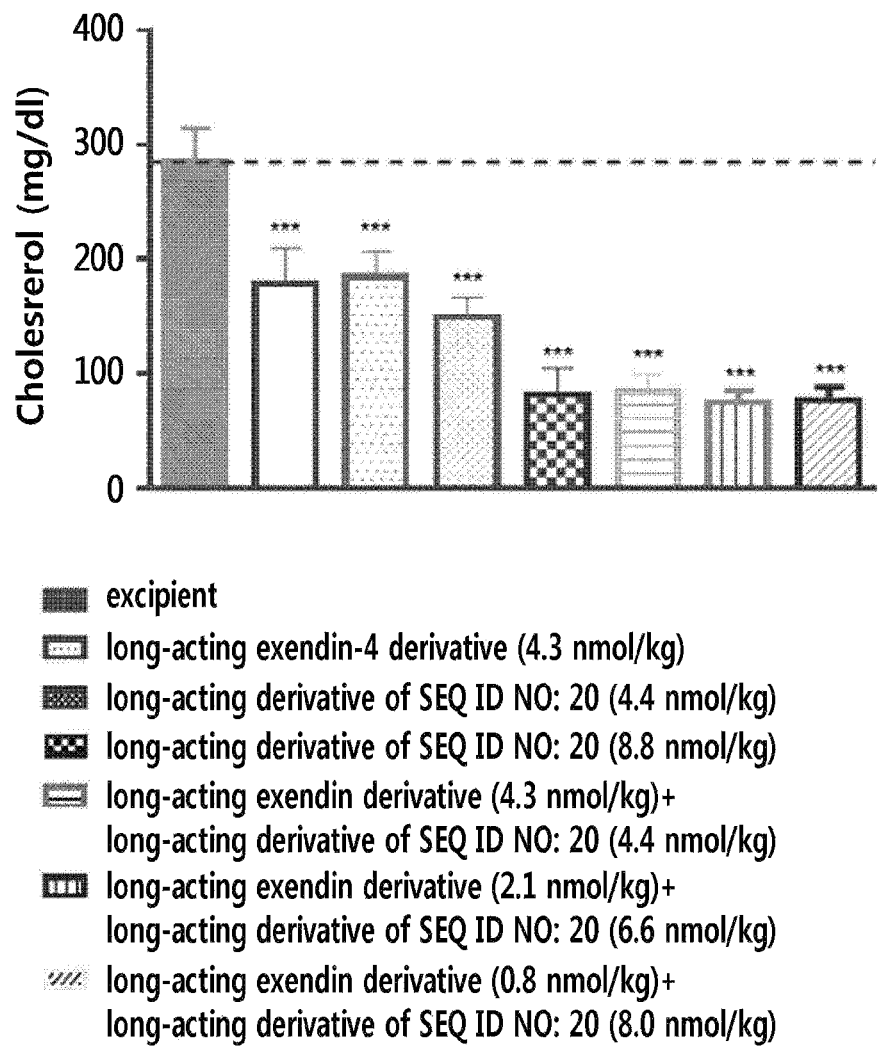
[Figure 5]

```
                          SEQUENCE LISTING

<160> NUMBER OF SEQ ID NOS: 48

<210> SEQ ID NO 1
<211> LENGTH: 29
<212> TYPE: PRT
<213> ORGANISM: homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: glucagon derivative

<400> SEQUENCE: 2

His Ser Gln Gly Thr Phe Thr Ser Asp Tyr Ser Lys Tyr Leu Asp Cys
1               5                   10                  15

Asp Arg Ala Gln Asp Phe Val Gln Trp Leu Met Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: glucagon derivative

<400> SEQUENCE: 3

His Ser Gln Gly Thr Phe Thr Ser Asp Tyr Ser Lys Tyr Leu Asp Cys
1               5                   10                  15

Glu Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: glucagon derivative

<400> SEQUENCE: 4

His Ser Gln Gly Thr Phe Thr Ser Asp Tyr Ser Lys Tyr Leu Asp Ser
1               5                   10                  15

Cys Asp Ala Gln Asp Phe Val Gln Trp Leu Met Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: glucagon derivative
```

```
<400> SEQUENCE: 5

His Ser Gln Gly Thr Phe Thr Ser Asp Tyr Ser Lys Tyr Leu Asp Ser
1               5                   10                  15

Cys Glu Ala Gln Asp Phe Val Gln Trp Leu Met Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: glucagon derivative

<400> SEQUENCE: 6

His Ser Gln Gly Thr Phe Thr Ser Asp Tyr Ser Lys Tyr Leu Asp Ser
1               5                   10                  15

Cys Glu Ala Asp Asp Phe Val Gln Trp Leu Met Asn Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: glucagon derivative

<400> SEQUENCE: 7

Tyr Ser Gln Gly Thr Phe Thr Ser Asp Tyr Ser Lys Tyr Leu Asp Ser
1               5                   10                  15

Cys Glu Ala Asp Asp Phe Val Gln Trp Leu Met Asn Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

Tyr Xaa Gln Gly Thr Phe Thr Ser Asp Tyr Ser Lys Tyr Leu Asp Ser
1               5                   10                  15

Cys Asp Ala Gln Asp Phe Val Gln Trp Leu Ile Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

Tyr Xaa Gln Gly Thr Phe Thr Ser Asp Tyr Ser Lys Tyr Leu Asp Ser
1               5                   10                  15

Cys Asp Ala Gln Asp Phe Val Val Trp Leu Ile Asn Thr
            20                  25
```

```
<210> SEQ ID NO 10
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

Tyr Xaa Gln Gly Thr Phe Thr Ser Asp Tyr Ser Lys Tyr Leu Asp Ser
1               5                   10                  15

Cys Asp Ala Asp Asp Phe Val Val Trp Leu Ile Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 11

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 12
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 12

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 13
```

Tyr Xaa Gln Gly Thr Phe Thr Ser Asp Tyr Ser Cys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 14

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 15

Tyr Xaa Gln Gly Thr Phe Thr Ser Asp Tyr Ser Lys Tyr Leu Cys Glu
1               5                   10                  15

Lys Arg Ala Gln Asp Phe Val Val Trp Leu Met Asn Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 16

Tyr Xaa Gln Gly Thr Phe Thr Ser Asp Tyr Ser Lys Tyr Leu Asp Cys
1               5                   10                  15

Arg Arg Ala Gln Val Phe Val Gln Trp Leu Met Arg Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 17

Tyr Xaa Gln Gly Thr Phe Thr Ser Asp Tyr Ser Lys Tyr Leu Asp Cys
1               5                   10                  15

Val Arg Ala Gln Asp Phe Val Gln Trp Leu Met Arg Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 18

Tyr Xaa Gln Gly Thr Phe Thr Ser Asp Tyr Ser Lys Tyr Leu Asp Ser
1               5                   10                  15

Arg Arg Ala Cys Asp Phe Arg Leu Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 19

Tyr Xaa Gln Gly Thr Phe Thr Ser Asp Tyr Ser Lys Tyr Leu Cys Glu
1               5                   10                  15

Lys Arg Ala Lys Glu Phe Val Gln Trp Leu Met Asn Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 20

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 21
<211> LENGTH: 29
<212> TYPE: PRT

```
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 22
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Tyr Leu Asp Glu
1               5                   10                  15

Lys Arg Cys Lys Glu Phe Val Gln Trp Leu Met Asn Thr
            20                  25

<210> SEQ ID NO 23
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Cys Asp Glu
1               5                   10                  15

Lys Arg Ala Lys Glu Phe Val Gln Trp Leu Met Asn Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
```

<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Met Asn Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 25

Tyr Xaa Gln Gly Thr Phe Thr Ser Asp Tyr Ser Lys Tyr Leu Asp Glu
1               5                   10                  15

Lys Arg Ala Lys Cys Phe Val Gln Trp Leu Met Asn Thr
            20                  25

<210> SEQ ID NO 26
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 26

Trp Xaa Gln Gly Thr Phe Thr Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 27

Tyr Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 28

Trp Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 29
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

Tyr Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25

<210> SEQ ID NO 30
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

Trp Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25

```
<210> SEQ ID NO 31
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (17)..(21)
<223> OTHER INFORMATION: amino acids at positions 17 and 21 form a ring

<400> SEQUENCE: 31

Tyr Xaa Gln Gly Thr Phe Thr Ser Asp Tyr Ser Lys Tyr Leu Asp Cys
1               5                   10                  15
Lys Arg Ala Lys Glu Phe Val Gln Trp Leu Met Asn Thr
            20                  25

<210> SEQ ID NO 32
<211> LENGTH: 28
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (15)..(19)
<223> OTHER INFORMATION: amino acids at positions 15 and 19 form a ring

<400> SEQUENCE: 32

Ser Gln Gly Thr Phe Thr Ser Asp Tyr Ser Lys Tyr Leu Asp Glu Cys
1               5                   10                  15
Arg Ala Lys Glu Phe Val Gln Trp Leu Met Asn Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 33

Tyr Xaa Gln Gly Thr Phe Thr Ser Asp Tyr Ser Lys Tyr Leu Asp Ser
1               5                   10                  15
Arg Arg Ala Gln Asp Phe Val Gln Trp Leu Met Asn Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring
```

-continued

```
<400> SEQUENCE: 34

Trp Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

Tyr Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

Tyr Xaa Gln Gly Thr Phe Thr Ser Asp Cys Ser Lys Tyr Leu Asp Glu
1               5                   10                  15

Arg Arg Ala Lys Glu Phe Val Gln Trp Leu Met Asn Thr
            20                  25

<210> SEQ ID NO 37
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

Tyr Xaa Gln Gly Thr Phe Thr Ser Asp Tyr Ser Lys Tyr Leu Asp Glu
1               5                   10                  15

Arg Arg Ala Lys Glu Phe Val Gln Trp Leu Met Asn Thr Cys
            20                  25                  30
```

<210> SEQ ID NO 38
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 38

Tyr Xaa Gln Gly Thr Phe Cys Ser Asp Tyr Ser Lys Tyr Leu Asp Glu
1               5                   10                  15

Arg Arg Ala Lys Glu Phe Val Gln Trp Leu Met Asn Thr
            20                  25

<210> SEQ ID NO 39
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 39

Tyr Xaa Gln Gly Thr Phe Val Ser Asp Cys Ser Lys Tyr Leu Asp Glu
1               5                   10                  15

Arg Arg Ala Lys Asp Phe Val Gln Trp Leu Met Asn Thr
            20                  25

<210> SEQ ID NO 40
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 40

Tyr Xaa Gln Gly Thr Phe Val Ser Asp Tyr Ser Lys Tyr Leu Asp Glu
1               5                   10                  15

Arg Arg Ala Lys Asp Phe Val Gln Trp Leu Met Asn Thr Cys
            20                  25                  30

<210> SEQ ID NO 41
<211> LENGTH: 29
<212> TYPE: PRT
<213> ORGANISM: Artificial Sequence
<220> FEATURE:

```
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 41

Tyr Xaa Gln Gly Thr Phe Cys Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 42

Tyr Xaa Gln Gly Thr Phe Cys Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 43

Tyr Xaa Gln Gly Thr Phe Thr Ser Asp Cys Ser Lys Tyr Leu Asp Ser
1               5                   10                  15

Arg Arg Ala Gln Asp Phe Val Gln Trp Leu Met Asn Thr
            20                  25

<210> SEQ ID NO 44
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 44

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30
```

```
<210> SEQ ID NO 45
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (1)
<223> OTHER INFORMATION: Xaa is histidine, desamino-histidyl,
      N-dimethyl-histidyl, beta-hydroxy imidazopropionyl,
      4-imidazoacetyl, beta-carboxy imidazopropionyl, tryptophan, or
      tyrosine, or is absent
<220> FEATURE:
<221> NAME/KEY: MISC_FEATURE
<222> LOCATION: (2)
<223> OTHER INFORMATION: Xaa is alpha-methyl-glutamic acid,
      aminoisobutyric acid (Aib), D-alanine, glycine, Sar
      (N-methylglycine), serine, or D-serine
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (13)
<223> OTHER INFORMATION: Xaa is tyrosine or cysteine
<220> FEATURE:
<221> NAME/KEY: MISC_FEATURE
<222> LOCATION: (14)
<223> OTHER INFORMATION: Xaa is leucine or cysteine
<220> FEATURE:
<221> NAME/KEY: MISC_FEATURE
<222> LOCATION: (15)
<223> OTHER INFORMATION: Xaa is aspartic acid, glutamic acid, or
      cysteine
<220> FEATURE:
<221> NAME/KEY: MISC_FEATURE
<222> LOCATION: (16)
<223> OTHER INFORMATION: Xaa is glutamic acid, aspartic acid, serine,
      alpha-methyl-glutamic acid, or cysteine, or is absent;
<220> FEATURE:
<221> NAME/KEY: MISC_FEATURE
<222> LOCATION: (17)
<223> OTHER INFORMATION: Xaa is aspartic acid, glutamine, glutamic acid,
      lysine, arginine, serine, cysteine, or valine, or is absent
<220> FEATURE:
<221> NAME/KEY: MISC_FEATURE
<222> LOCATION: (18)
<223> OTHER INFORMATION: Xaa is alanine, aspartic acid, glutamic acid,
      arginine, valine, or cysteine, or is absent
<220> FEATURE:
<221> NAME/KEY: MISC_FEATURE
<222> LOCATION: (19)
<223> OTHER INFORMATION: Xaa is alanine, arginine, serine, valine, or
      cysteine, or is absent
<220> FEATURE:
<221> NAME/KEY: MISC_FEATURE
<222> LOCATION: (20)
<223> OTHER INFORMATION: Xaa is lysine, histidine, glutamine, aspartic
      acid, lysine, arginine, alpha-methyl-glutamic acid, or cysteine,
      or is absent
<220> FEATURE:
<221> NAME/KEY: MISC_FEATURE
<222> LOCATION: (21)
<223> OTHER INFORMATION: Xaa is aspartic acid, glutamic acid, leucine,
      valine, or cysteine, or is absent
<220> FEATURE:
<221> NAME/KEY: MISC_FEATURE
<222> LOCATION: (23)
<223> OTHER INFORMATION: Xaa is isoleucine, valine, or arginine, or is
```

```
              absent
<220> FEATURE:
<221> NAME/KEY: MISC_FEATURE
<222> LOCATION: (24)
<223> OTHER INFORMATION: Xaa is valine, arginine, alanine, cysteine,
      glutamic acid, lysine, glutamine, alpha-methyl-glutamic acid, or
      leucine, or is absent;
<220> FEATURE:
<221> NAME/KEY: MISC_FEATURE
<222> LOCATION: (27)
<223> OTHER INFORMATION: Xaa is isoleucine, valine, alanine, lysine,
      methionine, glutamine, or arginine, or is absent
<220> FEATURE:
<221> NAME/KEY: MISC_FEATURE
<222> LOCATION: (28)
<223> OTHER INFORMATION: Xaa is glutamine, lysine, asparagine, or
      arginine, or is absent
<220> FEATURE:
<221> NAME/KEY: MISC_FEATURE
<222> LOCATION: (29)
<223> OTHER INFORMATION: Xaa is lysine, alanine, glycine, or threonine,
      or is absent
<220> FEATURE:
<221> NAME/KEY: MISC_FEATURE
<222> LOCATION: (30)
<223> OTHER INFORMATION: Xaa is cysteine, or is absent

<400> SEQUENCE: 45

Xaa Xaa Gln Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Xaa Xaa
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (15)
<223> OTHER INFORMATION: Xaa is aspartic acid or cysteine
<220> FEATURE:
<221> NAME/KEY: MISC_FEATURE
<222> LOCATION: (16)
<223> OTHER INFORMATION: Xaa is glutamic acid or serine
<220> FEATURE:
<221> NAME/KEY: MISC_FEATURE
<222> LOCATION: (17)
<223> OTHER INFORMATION: Xaa is lysine or arginine
<220> FEATURE:
<221> NAME/KEY: MISC_FEATURE
<222> LOCATION: (20)
<223> OTHER INFORMATION: Xaa is glutamine or lysine
<220> FEATURE:
<221> NAME/KEY: MISC_FEATURE
<222> LOCATION: (21)
<223> OTHER INFORMATION: Xaa is aspartic acid or glutamic acid
<220> FEATURE:
```

```
<221> NAME/KEY: MISC_FEATURE
<222> LOCATION: (24)
<223> OTHER INFORMATION: Xaa is valine or glutamine
<220> FEATURE:
<221> NAME/KEY: MISC_FEATURE
<222> LOCATION: (30)
<223> OTHER INFORMATION: Xaa is cysteine or is absent

<400> SEQUENCE: 46

Tyr Xaa Gln Gly Thr Phe Xaa Ser Asp Xaa Ser Xaa Tyr Leu Xaa Xaa
1               5                   10                  15

Xaa Arg Ala Xaa Xaa Phe Val Xaa Trp Leu Met Asn Thr Xaa
            20              25                  30

<210> SEQ ID NO 47
<211> LENGTH: 34
<212> TYPE: DNA
<213> ORGANISM: Artificial Sequence
<220> FEATURE:
<223> OTHER INFORMATION: forward primer

<400> SEQUENCE: 47
cagcgacacc gaccgtcccc ccgtacttaa ggcc                           34

<210> SEQ ID NO 48
<211> LENGTH: 32
<212> TYPE: DNA
<213> ORGANISM: Artificial Sequence
<220> FEATURE:
<223> OTHER INFORMATION: reverse primer

<400> SEQUENCE: 48
ctaaccgact ctcggggaag actgagctcg cc                             32
```

GLUCAGON DERIVATIVE AND A COMPOSITION COMPRISING A LONG ACTING CONJUGATE OF THE SAME

CROSS REFERENCE TO RELATED APPLICATIONS

This application is a National Stage of International Application No. PCT/KR2016/006984 filed Jun. 29, 2016, claiming priority based on Korean Patent Application No. 10-2015-0093265, filed Jun. 30, 2015, the contents of all of which are incorporated herein by reference in their entirety.

TECHNICAL FIELD

The present invention relates to a glucagon derivative, a long-acting conjugate of the glucagon derivative, and a use thereof.

BACKGROUND ART

Due to recent economic growth and changes in dietary habits, etc., the incidence of metabolic syndrome-associated diseases including various diseases such as obesity, hyperlipidemia, hypertension, arteriosclerosis, hyperinsulinemia, diabetes, and liver diseases is rapidly increasing. These diseases may occur independently but in general they mostly occur in close relationship with each other, being accompanied by various symptoms.

In particular, according to the World Health Organization (WHO), more than one billion adults are overweight worldwide, among them over 3 million are clinically obese, and 250,000 people die every year in Europe and more than 2.5 million people worldwide die every year due to overweight-related diseases.

Overweight and obesity are responsible for increasing blood pressure and cholesterol levels and causing or worsening various diseases, such as cardiac diseases, diabetes, arthritis, etc. In addition, the problem of obesity is also becoming a major cause in the increased incidence of arteriosclerosis, hypertension, hyperlipidemia, or heart diseases in children or teenagers as well as in adults.

Although obesity is a severe condition that causes various diseases worldwide as described above, it is thought to be overcome by individual effort, and it is also believed that obese patients lack self-control. However, obesity is not easy to treat, because it is a complex disease associated with the mechanisms of appetite control and energy metabolism. Accordingly, the treatment of obesity requires not only the efforts of obese patients, but also a method capable of treating abnormal mechanisms associated with appetite control and energy metabolism. Thus, efforts have been made to develop drugs for treating the abnormal mechanisms.

As a result of these efforts, drugs such as Rimonabant® (Sanofi-Aventis), Sibutramin® (Abbott), Contrave® (Takeda), Orlistat® (Roche), etc have been developed, but they have the disadvantages of serious adverse effects or very weak anti-obesity effects. For example, according to a report, Rimonabant® shows a side-effect of central nervous system disorder, Sibutramine® and Contrave® show cardiovascular side-effects, and Orlistat® shows only about 4 kg of weight loss when taken for one year. Accordingly, there are no therapeutic agents for obesity which can be prescribed safely for obese patients.

Many extensive studies have been made to develop novel therapeutic agents for obesity which can resolve the problems of the conventional anti-obesity drugs. Recently, glucagon derivatives have received much attention. Glucagon is produced by the pancreas when blood glucose levels drop as a result of other medications or diseases, or hormone or enzyme deficiencies. Glucagon sends a signal for glycogen breakdown in the liver and a subsequent glucose release and plays a role in increasing blood glucose levels to a normal range. In addition to the effect of increasing the blood glucose levels, glucagon suppresses appetite and activates hormone-sensitive lipase of adipocytes to facilitate lipolysis, thereby showing an anti-obesity effect. However, the use of glucagon as a therapeutic agent has been limited because it has a low solubility and it is precipitated at a neutral pH.

Accordingly, the glucagon with improved properties alone can be effectively used for the treatment of severe hypoglycemia, nonalcoholic steatohepatitis (NASH), dyslipidemia, etc., due to its activities of fat decomposition and β-oxydation in the liver.

One of the glucagon derivatives, glucagon-like peptide-1 (GLP-1), is under development as a therapeutic agent for treating hyperglycemia in patients with diabetes. GLP-1 has the functions of stimulating insulin synthesis and secretion, inhibiting glucagon secretion, slowing gastric emptying, increasing glucose utilization, and inhibiting food intake.

Exendin-4, prepared from lizard venom and having an amino acid homology of about 50% with GLP-1, was also reported to activate the GLP-1 receptor, thereby improving hyperglycemia in patients with diabetes (*J Biol Chem.* 1992 Apr. 15; 267 (11): 7402-5). However, anti-obesity drugs containing GLP-1 are reported to show side-effects such as vomiting and nausea.

As an alternative to GLP-1, therefore, much attention has been focused on oxyntomodulin, which can bind to both receptors of the two peptides, GLP-1 and glucagon. Oxyntomodulin is a peptide prepared from a glucagon precursor, pre-glucagon, and has the functions of inhibiting food intake and enhancing satiety of GLP-1, and has lipolytic activity like glucagon, thus increasing its potency in anti-obesity therapy.

However, oxyntomodulin or derivatives thereof have a serious drawback in that an excess amount of the drug should be administered daily because they have low efficacy and a short in vivo half-life.

Additionally, when both activities of GLP-1 and glucagon are present in a single peptide, the activity ratio thereof becomes fixed, and thus it is difficult to use a dual agonist with various ratios. Accordingly, a combined therapy capable of using various activity ratios by adjusting the contents of GLP-1 and glucagon may be more effective. However, for the combined therapy, it is required to improve the physical characteristics of glucagon, which aggregates at a neutral pH and precipitates with time, thus showing poor solubility.

Under these circumstances, the present inventors have developed glucagon derivatives with partial modifications of the amino acid sequence of glucagon for improving the therapeutic effects of glucagon on hypoglycemia and obesity by improving the physical properties of glucagon, and have discovered that these glucagon derivatives, due to the altered pI values which are different from that of native glucagon, have improved solubility and higher stability at a neutral pH and have confirmed that the developed glucagon derivative activates its receptors in in vitro assay, thereby completing the present invention.

DISCLOSURE

Technical Problem

An object of the present invention is to provide a pharmaceutical composition for treating or preventing metabolic syndrome, containing a glucagon derivative and at least one compound or material having a therapeutic activity for metabolic syndrome.

Another object of the present invention is to provide a novel glucagon derivative.

Still another object of the present invention is to provide an isolated polynucleotide encoding the glucagon derivative, a vector including the polynucleotide, and an isolated cell including the polynucleotide or the vector.

Still another object of the present invention is to provide an isolated conjugate in which a glucagon derivative and a biocompatible material which is capable of increasing in vivo half-life are linked.

Still another object of the present invention is to provide a composition containing the glucagon derivative and the isolated conjugate.

Still another object of the present invention is to provide a pharmaceutical composition for treating or preventing hypoglycemia or metabolic syndrome, containing the glucagon derivative or the isolated conjugate.

Still another object of the present invention is to provide a method for preventing or treating hypoglycemia or metabolic syndrome including administering the above composition to the subject in need thereof.

Still another object of the present invention is to provide use of the glucagon derivative or the isolated conjugate or the composition in the preparation of a medicament (or a pharmaceutical composition) for preventing or treating hypoglycemia or metabolic syndrome.

Technical Solution

In order to achieve the above objects, an aspect of the present invention provides a pharmaceutical composition for treating or preventing metabolic syndrome containing a glucagon derivative and at least one compound or material which has a therapeutic activity for metabolic syndrome.

More specifically, an aspect of the present invention provides a pharmaceutical composition for treating or preventing metabolic syndrome, which contains: i) a peptide including the amino acid sequence of the following General Formula 1, and ii) at least one compound or material having a therapeutic activity for metabolic syndrome:

(General Formula 1, SEQ ID NO: 45)
X1-X2-QGTF-X7-SD-X10-S-X12-X13-X14-X15-X16-X17-

X18-X19-X20-X21-F-X23-X24-W-L-X27-X28-X29-X30

In General Formula 1,

X1 is histidine, desamino-histidyl, N-dimethyl-histidyl, β-hydroxy imidazopropionyl, 4-imidazoacetyl, β-carboxy imidazopropionyl, tryptophan, or tyrosine, or is absent;

X2 is α-methyl-glutamic acid, aminoisobutyric acid (Aib), D-alanine, glycine, Sar(N-methylglycine), serine, or D-serine;

X7 is threonine, valine, or cysteine;
X10 is tyrosine or cysteine;
X12 is lysine or cysteine;
X13 is tyrosine or cysteine;
X14 is leucine or cysteine;
X15 is aspartic acid, glutamic acid, or cysteine;
X16 is glutamic acid, aspartic acid, serine, α-methyl-glutamic acid, or cysteine, or is absent;
X17 is aspartic acid, glutamine, glutamic acid, lysine, arginine, serine, cysteine, or valine, or is absent;

X18 is alanine, aspartic acid, glutamic acid, arginine, valine, or cysteine, or is absent;
X19 is alanine, arginine, serine, valine, or cysteine, or is absent;
X20 is lysine, histidine, glutamine, aspartic acid, lysine, arginine, α-methyl-glutamic acid, or cysteine, or is absent;
X21 is aspartic acid, glutamic acid, leucine, valine, or cysteine, or is absent;
X23 is isoleucine, valine, or arginine, or is absent;
X24 is valine, arginine, alanine, cysteine, glutamic acid, lysine, glutamine, α-methyl-glutamic acid, or leucine, or is absent;
X27 is isoleucine, valine, alanine, lysine, methionine, glutamine, or arginine, or is absent;
X28 is glutamine, lysine, asparagine, or arginine, or is absent;
X29 is lysine, alanine, glycine, or threonine, or is absent; and
X30 is cysteine, or is absent;
with the proviso that when the amino acid sequence of General Formula 1 is identical to SEQ ID NO: 1, it is excluded.

In another specific embodiment,
in General Formula 1,
X1 is histidine, tryptophan, or tyrosine, or is absent;
X2 is serine or aminoisobutyric acid (Aib);
X7 is threonine, valine, or cysteine;
X10 is tyrosine or cysteine;
X12 is lysine or cysteine;
X13 is tyrosine or cysteine;
X14 is leucine or cysteine;
X15 is aspartic acid or cysteine;
X16 is glutamic acid, serine, or cysteine;
X17 is aspartic acid, glutamic acid, lysine, arginine, serine, cysteine, or valine;
X18 is aspartic acid, glutamic acid, arginine, or cysteine;
X19 is alanine or cysteine;
X20 is glutamine, aspartic acid, lysine, or cysteine;
X21 is aspartic acid, glutamic acid, leucine, valine, or cysteine;
X23 is isoleucine, valine, or arginine;
X24 is valine, arginine, alanine, glutamic acid, lysine, glutamine, or leucine;
X27 is isoleucine, valine, alanine, methionine, glutamine, or arginine;
X28 is glutamine, lysine, asparagine, or arginine;
X29 is threonine; and
X30 is cysteine or is absent.

In still another specific embodiment, in General Formula 1,
X1 is histidine, tryptophan, or tyrosine, or is absent;
X2 is serine or aminoisobutyric acid (Aib);
X7 is threonine, valine, or cysteine;
X10 is tyrosine or cysteine;
X12 is lysine or cysteine;
X13 is tyrosine or cysteine;
X14 is leucine or cysteine;
X15 is aspartic acid or cysteine;
X16 is glutamic acid, serine, or cysteine;
X17 is aspartic acid, glutamic acid, lysine, arginine, serine, cysteine, or valine;
X18 is aspartic acid, glutamic acid, arginine, or cysteine;
X19 is alanine or cysteine;
X20 is glutamine, aspartic acid, or lysine;
X21 is aspartic acid or glutamic acid;
X23 is valine;
X24 is valine or glutamine;

X27 is isoleucine or methionine;
X28 is asparagine or arginine;
X29 is threonine; and
X30 is cysteine or is absent.

In still another specific embodiment, in General Formula 1,

X1 is tyrosine, X2 is aminoisobutyric acid (Aib);
X7 is threonine;
X10 is tyrosine;
X12 is lysine;
X13 is tyrosine;
X14 is leucine;
X15 is aspartic acid or cysteine;
X16 is glutamic acid, serine, or cysteine;
X17 is lysine or arginine;
X18 is arginine;
X19 is alanine;
X20 is glutamine, cysteine, or lysine;
X21 is aspartic acid, cysteine, valine, or glutamic acid;
X23 is valine;
X24 is valine or arginine;
X27 is methionine;
X28 is asparagine or arginine;
X29 is threonine; and
X30 is absent.

In still another specific embodiment, the above peptide is characterized in that it is a peptide including the amino acid sequence of the following General Formula 2:

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine or is absent,
wherein, among the peptides including the amino acid sequence of General Formula 2, the peptides corresponding to SEQ ID NOS: 14, 19, 20, 25, 27, 31, and 33 may be excluded.

In still another specific embodiment, the peptide including the amino acid sequence of General Formula 1 is characterized in that it has a pI value different to that of native glucagon, e.g., a pI of 6.5 or less, or a pI of 7.0 or higher.

In still another specific embodiment, the peptide including the amino acid sequence of General Formula 1 is characterized in that at least one amino acid pair among the amino acid pairs of X10 and X14, X12 and X16, X16 and X20, X17 and X21, X20 and X24, and X24 and X28 in General Formula 1 is substituted with glutamic acid or lysine, which is capable of forming a ring, respectively.

In still another specific embodiment, the peptide including the amino acid sequence of General Formula 1 is characterized in that the amino acid pair of X12 and X16 or the amino acid pair of X16 and X20 is respectively substituted with glutamic acid or lysine, which is capable of forming a ring.

In still another specific embodiment, the peptide including the amino acid sequence of General Formula 1 is characterized in that at least one amino acid pair among the amino acid pairs of X10 and X14, X12 and X16, X16 and X20, X17 and X21, X20 and X24, and X24 and X28 in General Formula 1 forms a ring (e.g., a lactam ring).

In still another specific embodiment, the peptide including the amino acid sequence of General Formula 1 is characterized in that the C-terminus of the peptide is amidated.

In still another specific embodiment, the peptide including the amino acid sequence of the following General Formula 1 is characterized in that it is a glucagon derivative capable of activating a glucagon receptor.

In still another specific embodiment, the peptide is characterized in that it includes an amino acid sequence selected from the group consisting of SEQ ID NOS: 2 to 44.

In still another specific embodiment, the peptide is characterized in that it includes an amino acid sequence selected from the group consisting of SEQ ID NOS: 2 to 13, 15, 17, 20 to 24, 26 to 30, and 32 to 44.

In still another specific embodiment, the peptide is characterized in that it includes an amino acid sequence of SEQ ID NO: 12 or SEQ ID NO: 20.

In still another specific embodiment, the compound or material having a therapeutic activity for metabolic syndrome is characterized in that it is selected from the group consisting of an insulinotropic peptide, a glucagon-like peptide-1 (GLP-1) receptor agonist, a leptin receptor agonist, a dipeptidyl peptidase-IV (DPP-IV) inhibitor, a Y5 receptor antagonist, a melanin-concentrating hormone (MCH) receptor antagonist, a Y2/4 receptor agonist, a melanocortin 3/4 (MC 3/4) receptor agonist, a gastric/pancreatic lipase inhibitor, an agonist of 5-hydroxytryptamine receptor 2C (5HT2C), a β3A receptor agonist, an amylin receptor agonist, a ghrelin antagonist, a ghrelin receptor antagonist, a peroxisome proliferator-activated receptor alpha (PPARα) agonist, a peroxisome proliferator-activated receptor delta (PPARδ) agonist, a Farnesoid X receptor (FXR) agonist, an acetyl-CoA carboxylase inhibitor, a peptide YY, cholecystokinin (CCK), xenin, glicentin, obestatin, secretin, nesfatin, insulin, and a glucose-dependent insulinotropic peptide (GIP).

In still another specific embodiment, the insulinotropic peptide is characterized in that it is selected from the group consisting of GLP-1, exendin-3, exendin-4, an agonist thereof, a derivative thereof, a fragment thereof, a variant thereof, and a combination thereof.

In still another specific embodiment, the insulinotropic peptide is characterized in that it is an insulinotropic peptide derivative in which the N-terminal histidine residue of the insulinotropic peptide is substituted with one selected from the group consisting of desamino-histidyl, N-dimethyl-histidyl, β-hydroxy imidazopropionyl, 4-imidazoacetyl, and β-carboxy imidazopropionyl.

In still another specific embodiment, the insulinotropic peptide is characterized in that it is selected from the group consisting of a native exendin-4; an exendin-4 derivative in which the N-terminal amine group of exendin-4 is deleted; an exendin-4 derivative in which the N-terminal amine group of exendin-4 is substituted with a hydroxyl group; an exendin-4 derivative in which the N-terminal amine group of exendin-4 is modified with a dimethyl group; an exendin-4 derivative in which the α-carbon of the $1^{st}$ amino acid of exendin-4, histidine, is deleted; an exendin-4 derivative in which the $12^{th}$ amino acid of exendin-4, lysine, is substituted with serine, and an exendin-4 derivative in which the $12^{th}$ amino acid of exendin-4, lysine, is substituted with arginine.

In still another specific embodiment, the peptide including the amino acid sequence of General Formula 1 is characterized in that the peptide including the amino acid sequence of General Formula 1 is in the form of a long-acting conjugate to which a biocompatible material capable of increasing in vivo half-life of the peptide is linked; and the insulinotropic peptide is in the form of a long-acting conjugate to which a biocompatible material capable of increasing in vivo half-life of the insulinotropic peptide is linked.

In still another specific embodiment, the biocompatible material is characterized in that it is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, and a polymer.

In still another specific embodiment, the peptide including the amino acid sequence of General Formula 1 and the insulinotropic peptide are characterized in that they are respectively linked to a biocompatible material by a linker selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, fatty acid, a polymer, a low molecular weight compound, a nucleotide, and a combination thereof.

In still another specific embodiment, the biocompatible material is characterized in that it is an FcRn-binding material, and the peptide including the amino acid sequence of General Formula 1 and the insulinotropic peptide are respectively linked to a biocompatible material by a peptide linker or a non-peptide linker selected from the group consisting of polyethylene glycol, polypropylene glycol, an ethylene glycol-propylene glycol copolymer, polyoxyethylated polyol, polyvinyl alcohol, a polysaccharide, polyvinyl ethyl ether, dextran, a biodegradable polymer such as polylactic acid (PLA) and polylactic-glycolic acid (PLGA), lipid polymer, chitin, hyaluronic acid, and a combination thereof.

In still another specific embodiment, the FcRn-binding material is characterized in that it is a polypeptide including an immunoglobulin Fc region.

In still another specific embodiment, the immunoglobulin Fc region is characterized in that it is aglycosylated.

In still another specific embodiment, the immunoglobulin Fc region is characterized in that it is selected from the group consisting of:

(a) a CH1 domain, a CH2 domain, a CH3 domain, and a CH4 domain;
(b) a CH1 domain and a CH2 domain;
(c) a CH1 domain and a CH3 domain;
(d) a CH2 domain and a CH3 domain;
(e) a combination between one or two or more domains among a CH1 domain, a CH2 domain, a CH3 domain, and a CH4 domain and an immunoglobulin hinge region or a part of the hinge region; and
(f) a dimer between each domain of the heavy chain constant region and the light chain constant region.

In still another specific embodiment, the polypeptide including the immunoglobulin Fc region is in the form of a dimer.

In still another specific embodiment, the immunoglobulin Fc region is characterized in that it is a native Fc derivative in which the region capable of forming a disulfide bond is deleted, a native Fc derivative in which a part of the amino acid(s) in the N-terminus is deleted, a native Fc derivative in which a methionine is added to the N-terminus, a native Fc derivative in which a complement-binding site is deleted, or a native Fc derivative in which an antibody dependent cell mediated cytotoxicity (ADCC) site is deleted.

In still another specific embodiment, the immunoglobulin Fc region is characterized in that it is an Fc region derived from an immunoglobulin selected from the group consisting of IgG, IgA, IgD, IgE, and IgM.

In still another specific embodiment, the immunoglobulin Fc region is characterized in that it is an IgG4 Fc region.

In still another specific embodiment, the immunoglobulin Fc region is characterized in that it is an aglycosylated Fc region derived from human IgG4.

In still another specific embodiment, the non-peptide linker is characterized in that it is linked to the cysteine residue of a peptide including the amino acid sequence of General Formula 1.

In still another specific embodiment, the non-peptide linker is characterized in that both ends of the non-peptide linker are respectively linked to an amine group or a thiol group of a peptide, which includes the amino acid sequence of General Formula 1, or an insulinotropic peptide, and a biocompatible material.

In still another specific embodiment, the metabolic syndrome is characterized in that it is selected from the group consisting of impaired glucose tolerance, hypercholesterolemia, dyslipidemia, obesity, diabetes, hypertension, non-alcoholic steatohepatitis (NASH), atherosclerosis caused by dyslipidemia, atherosclerosis, arteriosclerosis, coronary heart disease, and stroke.

In another aspect, the present invention provides a novel glucagon derivative.

In a specific embodiment, the glucagon derivative is characterized in that it is an isolated peptide including the amino acid sequence of the following General Formula 2:

(General Formula 2, SEQ ID NO: 46)
Y-Aib-QGTF-X7-SD-X10-S-X12-Y-L-X15-X16-X17-R-A-

X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine or is absent,
wherein, among the peptides including the amino acid sequence of General Formula 2, the peptides corresponding to SEQ ID NOS: 14, 19, 20, 25, 27, 31, and 33 may be excluded.

In still another specific embodiment, the peptide including the amino acid sequence of General Formula 2 is characterized in that the amino acid pair of X16 and X20 is substituted with glutamic acid or lysine, which is capable of forming a ring.

In still another specific embodiment, the peptide including the amino acid sequence of General Formula 2 is characterized in that the C-terminus of the peptide is amidated.

In still another specific embodiment, the peptide is characterized in that it is a glucagon derivative capable of activating a glucagon receptor.

In still another specific embodiment, the peptide is characterized in that it includes an amino acid sequence selected from the group consisting of SEQ ID NOS: 12, 13, 15, and 36 to 44.

In still another specific embodiment, the peptide is characterized in that it includes the amino acid sequence of SEQ ID NO: 12.

In still another aspect, the present invention provides an isolated polynucleotide encoding the glucagon derivative, a vector including the polynucleotide, and an isolated cell including the polynucleotide or the vector.

In still another aspect, the present invention provides an isolated conjugate in which a glucagon derivative and a biocompatible material capable of increasing in vivo half-life are linked.

In a specific embodiment, the biocompatible material is characterized in that the biocompatible material is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, and a polymer.

In a specific embodiment, the isolated peptide is characterized in that it is linked to a biocompatible material by a linker selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, fatty acid, a polymer, a low molecular weight compound, a nucleotide, and a combination thereof.

In a specific embodiment, the biocompatible material is characterized in that it is an FcRn-binding material, and the isolated peptide and the insulinotropic peptide are respectively linked to a biocompatible material by a peptide linker or a non-peptide linker selected from the group consisting of polyethylene glycol, polypropylene glycol, an ethylene glycol-propylene glycol copolymer, polyoxyethylated polyol, polyvinyl alcohol, a polysaccharide, polyvinyl ethyl ether, dextran, a biodegradable polymer such as polylactic acid (PLA) or polylactic-glycolic acid (PLGA), lipid polymer, chitin, hyaluronic acid, and a combination thereof.

In a specific embodiment, the FcRn-binding material is characterized in that it is a polypeptide including an immunoglobulin Fc region.

In still another aspect, the present invention provides a composition including the glucagon derivative or the isolated conjugate.

In a specific embodiment, the composition is characterized in that it is a pharmaceutical composition for treating or preventing hypoglycemia or metabolic syndrome.

In still another aspect, the present invention provides a method for preventing or treating hypoglycemia or metabolic syndrome including administering the composition to the subject in need thereof.

In still another aspect, the present invention provides use of the glucagon derivative or the isolated conjugate or the composition in the preparation of a medicament (or a pharmaceutical composition) for preventing or treating hypoglycemia or metabolic syndrome.

Advantageous Effects

The glucagon derivatives of the present invention have improved physical properties compared to that of native glucagon and thus can be effectively used as a therapeutic agent for treating hypoglycemia by improving the compliance of patients. Additionally, the glucagon derivatives of the present invention can be effectively used for the prevention and treatment of hypoglycemia and metabolic syndrome such as obesity, diabetes, and nonalcoholic steatohepatitis (NASH).

DESCRIPTION OF DRAWINGS

FIG. 1 shows a graph illustrating the changes in body weight of obesity animal models (rats), which were prepared by high-fat diet, during a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats, at 3-day intervals for 15 days.

FIG. 2 shows a result illustrating the amount of mesenteric fat of obesity animal models (rats), which were prepared by high-fat diet, measured after a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats for 15 days ($*p<0.05$, $**p<0.01$ vs. vehicle by ANOVA test).

FIG. 3 shows a result illustrating the difference in liver weight of obesity animal models (rats), which were prepared by high-fat diet, measured after a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats for 15 days ($*p<0.01$, $*p<0.001$ vs. vehicle by ANOVA test).

FIG. 4 shows a graph illustrating the changes in body weight (BW) of obesity animal models (mice), which were prepared by high-fat diet, after a single or combined administration of a long-acting insulinotropic peptide conjugate (named as a long-acting exendin-4 derivative) and a long-acting glucagon derivative conjugate (named as a long-acting derivative of SEQ ID NO: 20) with an adjusted dose to the rats for 22 days.

FIG. 5 shows a result illustrating the changes in cholesterol content in blood of obesity animal models (mice), which were prepared by high-fat diet, after a single or combined administration of a long-acting insulinotropic peptide conjugate (named as a long-acting exendin-4 derivative) and a long-acting glucagon derivative conjugate (named as a long-acting derivative of SEQ ID NO: 20) with an adjusted dose to the rats for 22 days.

BEST MODE

The specific details of the present invention may be explained as follows. In particular, the explanations and embodiments disclosed in the present invention may be applied to other explanations and embodiments, respectively. That is, all combinations of various elements disclosed in the present invention belong to the scope of the present invention. Additionally, the scope of the present invention should not be limited by the specific descriptions described herein below.

Throughout the disclosure of the present invention, not only the conventional 1-letter codes and 3-letter codes for amino acids present in nature but also the 3-letter codes, such as Aib (α-aminoisobutyric acid), Sar(N-methylglycine) generally used for other amino acids, are used. Additionally, the amino acids mentioned in abbreviation in the present disclosure are described according to the IUPAC-IUB Nomenclature.

| alanine A | arginine R |
| asparagine N | aspartic acid D |
| cysteine C | glutamic acid E |
| glutamine Q | glycine G |
| histidine H | isoleucine I |
| leucine L | lysine K |
| methionine M | phenylalanine F |
| proline P | serine S |
| threonine T | tryptophan W |
| tyrosine Y | valine V |

An aspect of the present invention provides a composition containing a glucagon derivative and at least one compound or material having a therapeutic activity for metabolic syndrome, and more specifically, provides a pharmaceutical composition for treating or preventing metabolic syndrome containing a glucagon derivative and at least one compound or material having a therapeutic activity for metabolic syndrome.

The glucagon derivative according to the present invention includes a peptide having at least one difference in the amino acid sequence compared to native glucagon, a peptide in which the sequence of native glucagon is modified by modifying native glucagon, and a native glucagon mimetic that can activate glucagon receptors like native glucagon.

Such a glucagon derivative may be one having improved physical properties by having an altered pI relative to native glucagon. Additionally, the glucagon derivative may be one with improved solubility while maintaining the activity of activating glucagon receptors, but is not limited thereto.

Additionally, the glucagon derivative may be a non-naturally occurring glucagon.

In particular, native glucagon may have the following amino acid sequence:

```
                                       (SEQ ID NO: 1)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr
```

As used herein, the term "pI" or "isoelectric point" refers to the pH value at which a macromolecule such as a polypeptide has no net charge (0). In the case of a polypeptide with various charged functional groups, the net charge of the total polypeptide is "0" at a point where the pH value is the same as that of the pI. The net charge of the polypeptide at a pH higher than the pI will be negative while the net charge of the polypeptide at a pH lower than the pI will be positive.

The pI values may be determined on an immobilized pH gradient gel consisting of polyacrylamide, starch, or agarose by isoelectric electrophoresis, or may be estimated, for example, from an amino acid sequence using a pI/MW tool (e.g., expasy.org/tools/pi_tool.html; Gasteiger et al., 2003) in an ExPASy server. As used herein, the term "altered pI" refers to a pI which is different from that of native glucagon due to the substitution of a part of the amino acid sequence of native glucagon with an amino acid residue having a negative charge or a positive charge, i.e., a reduced or increased pI value. The peptide with such an altered pI can exhibit improved solubility and high stability at a neutral pH as a glucagon derivative.

More specifically, the glucagon derivative may have an altered pI value, not the pI value (6.8) of native glucagon, and even more specifically, a pI value of less than 6.8, more specifically, 6.7 or less, more specifically 6.5 or less, and additionally, a pI value exceeding 6.8, 7 or higher, more specifically, 7.5 or higher, but is not limited thereto, and any pI value different from that of native glucagon will belong to the scope of the present invention. In particular, when the pI value is different from that of native glucagon and thus exhibits an improved solubility at a neutral pH compared to that of native glucagon thus showing a low level of aggregation, it will particularly belong to the scope of the present invention.

More specifically, the glucagon derivative may have a pI value of from 4 to 6.5 and/or from 7 to 9.5, specifically from 7.5 to 9.5, and more specifically, from 8.0 to 9.3, but the pI value is not limited thereto. In this case, due to the lower or higher pI value compared to that of native glucagon, an improved solubility and high stability at a neutral pH compared to that of native glucagon can be exhibited.

Specifically, a derivative of native glucagon may be modified by any one method of substitution, addition, deletion, and modification, or a combination thereof in part of the amino acid of native glucagon.

Examples of the glucagon derivatives prepared by a combination of the above methods include a peptide which differs in at least one amino acid residue of the amino acid sequence compared to that of native glucagon and in which the N-terminal amino acid residue is deaminated, having the function of activating a glucagon receptor, but is not limited thereto, and the native glucagon derivatives can be prepared by a combination of various methods for preparing the derivatives.

Additionally, such modification for the preparation of native glucagon derivatives may include all of the modifications using L-type or D-type amino acids, and/or non-native type amino acids; and/or a modification of native sequence, for example, modification of a functional group, an intramolecular covalent bonding (e.g., a ring formation between side chains), methylation, acylation, ubiquitination, phosphorylation, aminohexanation, biotinylation, etc.

Additionally, the modification may also include all those where one or more amino acids are added to the amino and/or carboxy terminal of native glucagon.

During the substitution or addition of amino acids, not only the 20 amino acids commonly found in human proteins, but also atypical or non-naturally occurring amino acids can be used. Commercial sources of atypical amino acids may include Sigma-Aldrich, ChemPep Inc., and Genzyme Pharmaceuticals. The peptides including these amino acids and atypical peptide sequences may be synthesized and purchased from commercial suppliers, e.g., American Peptide Company, Bachem (USA), or Anygen (Korea).

Since glucagon has a pH of about 7, it is insoluble in a solution having a physiological pH (pH 4 to 8) and tends to precipitate at a neutral pH. In an aqueous solution with a pH of 3 or below, glucagon is dissolved at the initial stage but precipitates within one hour by forming a gel. Since the gelated glucagon mainly consists of β-sheet fibrils, the administration of the thus-precipitated glucagon via an injection needle or intravenous injection will block blood vessels, and thus is not suitable for use as an injection agent. In order to delay the precipitation process, acidic (pH 2 to 4) formulations are commonly used, and by doing so, glucagon can be maintained in a relatively non-aggregated state for a short period of time. However, glucagon can form fibrils very rapidly at a low pH, and thus these acidic formulations must be injected upon preparation.

In this regard, the present inventors have developed glucagon derivatives with extended action profiles by modifying the pI of native glucagon via substitution of amino acid residues having negative charges and positive charges. The glucagon derivatives of the present invention, by having an altered pI compared to that of native glucagon, are characterized in having improved solubility and/or high stability at a neutral pH, compared to that of native glucagon.

In a specific embodiment of the present invention, the glucagon derivative may be a peptide which includes the amino acid sequence of the following General Formula 1:

(General Formula 1, SEQ ID NO: 45)
X1-X2-QGTF-X7-SD-X10-S-X12-X13-X14-X15-X16-X17-

X18-X19-X20-X21-F-X23-X24-W-L-X27-X28-X29-X30

In the above Formula,

X1 is histidine, desamino-histidyl, N-dimethyl-histidyl, β-hydroxy imidazopropionyl, 4-imidazoacetyl, β-carboxy imidazopropionyl, tryptophan, or tyrosine, or is absent;

X2 is α-methyl-glutamic acid, aminoisobutyric acid (Aib), D-alanine, glycine, Sar(N-methylglycine), serine, or D-serine;

X7 is threonine, valine, or cysteine;

X10 is tyrosine or cysteine;

X12 is lysine or cysteine;

*273X13 is tyrosine or cysteine;

X14 is leucine or cysteine;

X15 is aspartic acid, glutamic acid, or cysteine;

X16 is glutamic acid, aspartic acid, serine, α-methyl-glutamic acid, or cysteine, or is absent;

X17 is aspartic acid, glutamine, glutamic acid, lysine, arginine, serine, cysteine, or valine, or is absent;

X18 is alanine, aspartic acid, glutamic acid, arginine, valine, or cysteine, or is absent;

X19 is alanine, arginine, serine, valine, or cysteine, or is absent;

X20 is lysine, histidine, glutamine, aspartic acid, lysine, arginine, α-methyl-glutamic acid, or cysteine, or is absent;

X21 is aspartic acid, glutamic acid, leucine, valine, or cysteine, or is absent;

X23 is isoleucine, valine, or arginine, or is absent;

X24 is valine, arginine, alanine, cysteine, glutamic acid, lysine, glutamine, α-methyl-glutamic acid, or leucine, or is absent;

X27 is isoleucine, valine, alanine, lysine, methionine, glutamine, or arginine, or is absent;

X28 is glutamine, lysine, asparagine, or arginine, or is absent;

X29 is lysine, alanine, glycine, or threonine, or is absent; and

X30 is cysteine or is absent;

with the proviso that when the amino acid sequence of General Formula 1 is identical to SEQ ID NO: 1, it is excluded.

In the above, when the amino acid sequence of General Formula 1 is identical to any amino acid sequence selected from the group consisting of SEQ ID NOS: 12, 13, 15, and 36 to 44, and in particular, to the amino acid sequence any of the amino acid sequences of SEQ ID NOS: 13, 15, 36, and 38 to 43, it may be possible that the peptide may be excluded from the scope of the peptides that include the amino acid sequence of General Formula 1, but is not limited thereto.

More specifically, in General Formula 1,

X1 is histidine, tryptophan, or tyrosine, or is absent;

X2 is serine or aminoisobutyric acid (Aib);

X7 is threonine, valine, or cysteine;

X10 is tyrosine or cysteine;

X12 is lysine or cysteine;

X13 is tyrosine or cysteine;

X14 is leucine or cysteine;

X15 is aspartic acid or cysteine;

X16 is glutamic acid, serine, or cysteine;

X17 is aspartic acid, glutamic acid, lysine, arginine, serine, cysteine, or valine;

X18 is aspartic acid, glutamic acid, arginine, or cysteine;

X19 is alanine or cysteine;

X20 is glutamine, aspartic acid, lysine, or cysteine;

X21 is aspartic acid, glutamic acid, leucine, valine, or cysteine;

X23 is isoleucine, valine, or arginine;

X24 is valine, arginine, alanine, glutamic acid, lysine, glutamine, or leucine;

X27 is isoleucine, valine, alanine, methionine, glutamine, or arginine;

X28 is glutamine, lysine, asparagine, or arginine;

X29 is threonine; and

X30 is cysteine or is absent with the proviso that when the amino acid sequence of General Formula 1 is identical to SEQ ID NO: 1, it is excluded.

For example, the peptide may be one which includes an amino acid sequence selected from the group consisting of SEQ ID NOS: 2 to 44, and specifically, one which (essentially) consists of an amino acid sequence selected from the group consisting of SEQ ID NOS: 2 to 44, but is not limited thereto.

Additionally, although described as "a peptide consisting of a particular SEQ ID NO" in the present invention, such expression does not exclude a mutation in the peptide that can occur by a meaningless sequence addition upstream or downstream of the amino acid sequence of the corresponding SEQ ID NO, or a naturally-occurring mutation therein, or a silent mutation therein, as long as the peptide having such mutation has an activity the same as or corresponding to that of the peptide which consists of an amino acid sequence of the corresponding SEQ ID NO. Even when the sequence addition or a mutation is present, it obviously belongs to the scope of the present invention.

In contrast, in another aspect, when the amino acid sequence of General Formula 1 is identical to the amino acid sequence selected from the group consisting of SEQ ID NOS: 12, 13, 15, and 36 to 44, and in particular, to any of the amino acid sequences of SEQ ID NOS: 13, 15, 36, and 38 to 43, the peptide may be possibly excluded from the scope of the peptides that include the amino acid sequence of General Formula 1, but is not limited thereto. Those described above may be also applied to other specific embodiments or aspects, but is not limited thereto.

Specifically, in General Formula 1,
X1 is histidine, tryptophan, or tyrosine, or is absent;
X2 is serine or aminoisobutyric acid (Aib);
X7 is threonine, valine, or cysteine;
X10 is tyrosine or cysteine;
X12 is lysine or cysteine;
X13 is tyrosine or cysteine;
X14 is leucine or cysteine;
X15 is aspartic acid or cysteine;
X16 is glutamic acid, serine or cysteine;
X17 is aspartic acid, glutamic acid, lysine, arginine, serine, cysteine, or valine;
X18 is aspartic acid, glutamic acid, arginine, or cysteine;
X19 is alanine or cysteine;
*332X20 is glutamine, aspartic acid, or lysine;
X21 is aspartic acid or glutamic acid;
X23 is valine;
X24 is valine or glutamine;
X27 is isoleucine or methionine;
X28 is asparagine or arginine;
X29 is threonine; and
X30 is cysteine or is absent
with the proviso that when the amino acid sequence of General Formula 1 is identical to SEQ ID NO: 1, it is excluded.

For example, the peptide may be one which includes an amino acid sequence selected from the group consisting of SEQ ID NOS: 2 to 13, 15, 17, 20 to 24, 26 to 30, and 32 to 44, and specifically, one which (essentially) consists of an amino acid sequence selected from the group consisting of SEQ ID NOS: 2 to 13, 15, 17, 20 to 24, 26 to 30, and 32 to 44, but is not limited thereto.

Specifically, in the General Formula 1,
X1 is tyrosine;
X2 is aminoisobutyric acid;
X7 is threonine;
X10 is tyrosine;
X12 is lysine;
*349X13 is tyrosine;
X14 is leucine;
X15 is aspartic acid or cysteine;
X16 is glutamic acid, serine, or cysteine;
X17 is lysine or arginine;
X18 is arginine;
X19 is alanine;
X20 is glutamine, cysteine, or lysine;
X21 is aspartic acid, cysteine, valine, or glutamic acid;
X23 is valine;
X24 is valine or arginine;
X27 is methionine;
X28 is asparagine or arginine;
X29 is threonine; and
X30 is absent.

For example, the peptide may be one which includes an amino acid sequence selected from the group consisting of SEQ ID NOS: 14, 16, 18, 19, 25 and 31, and specifically, one which (essentially) consists of an amino acid sequence selected from the group consisting of SEQ ID NOS: 14, 16, 18, 19, 25 and 31, but is not limited thereto.

More specifically, the peptide may be a peptide which includes the amino acid sequence of the following General Formula 2:

(General Formula 2, SEQ ID NO: 46)
Y-Aib-QGTF-X7-SD-X10-S-X12-Y-L-X15-X16-X17-R-A-

X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine or is absent,
with the proviso that when the amino acid sequence of General Formula 2 is identical to any one of SEQ ID NOS: 14, 19, 20, 25, 27, 31, and 33, it may be excluded, but it is not limited thereto.

For example, the peptide may be one which includes an amino acid sequence selected from the group consisting of SEQ ID NOS: 12, 13, 15, and 36 to 44, and specifically, one which (essentially) consists of an amino acid sequence selected from the group consisting of SEQ ID NOS: 12, 13, 15, and 36 to 44, but is not limited thereto. More specifically, the peptide may be one which includes an amino acid sequence of SEQ ID NO: 12 or SEQ ID NO: 20, or (essentially) consists of the corresponding amino acid sequence, but is not limited thereto.

Additionally, the peptide including the amino acid sequence of General Formula 1 or General Formula 2 may be one in which at least one amino acid pair among the amino acid pairs of X10 and X14, X12 and X16, X16 and X20, X17 and X21, X20 and X24, and X24 and X28 in General Formula 1 or General Formula 2 may be substituted with glutamic acid or lysine, which is capable of forming a ring, respectively, but is not limited thereto.

More specifically, the peptide including the amino acid sequence of General Formula 1 or General Formula 2 may be one in which the amino acid pair of X12 and X16 or the amino acid pair of X16 and X20 is respectively substituted with glutamic acid or lysine, which is capable of forming a ring.

More specifically, at least one amino acid pair among the amino acid pairs of X10 and X14, X12 and X16, X16 and X20, X17 and X21, X20 and X24, and X24 and X28 may be one which forms a ring (e.g., a lactam ring), but is not limited thereto.

In particular, the peptide may be modified in its amino terminus or carboxy terminus or protected by various organic groups for protecting the peptide from protein-cleaving enzymes in vivo while increasing its stability, for example, one in which its C-terminus is amidated.

Additionally, the peptide of the present invention may be synthesized by a method well known in the art, according to its length, e.g., by an automatic peptide synthesizer, and may be produced by genetic engineering technology.

Specifically, the peptide of the present invention may be prepared by a standard synthesis method, a recombinant expression system, or any other method known in the art. Accordingly, the glucagon derivative of the present invention may be synthesized by various methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining the peptide by linking the peptide fragments, and then recovering the peptide.

In a more specific example, a desired glucagon derivative may be produced by genetic manipulation, which includes preparing a fusion gene encoding a fusion protein, including a fusion partner and a glucagon derivative, transforming the resultant into a host cell, expressing in the form of a fusion protein, and cleaving the glucagon derivative from the fusion protein using a protease or a compound which is capable of protein cleavage followed by separation. For this purpose, for example, an amino acid residue-encoding DNA sequence that can be cleaved by a protease such as Factor Xa or enterokinase, CNBr, or a compound such as hydroxylamine, may be inserted between the fusion partner and a polynucleotide encoding a glucagon derivative.

In a specific embodiment of the present invention, it was confirmed that the peptide of the present invention has a different pI compared to that of native glucagon (see Table 1). As a result, the peptide of the present invention has improved solubility and higher stability at a neutral pH. Accordingly, the peptide of the present invention can increase patient compliance when used as a hypoglycemic agent and is also suitable for combined administration of the peptide with other anti-obesity agents, and thus can be effectively used for the prevention and treatment of hypoglycemia and obesity.

In this regard, the peptide of the present invention can provide an attractive therapeutic selection regarding hypoglycemia, obesity, or associated diseases thereof.

For example, the peptide of the present invention is a major insulin response-controlling hormone, and can be effectively used for the treatment of severe hypoglycemia in diabetic patients.

Additionally, the peptide of the present invention may be used as a pharmaceutical medicament not only for preventing body weight increase, promotion of body weight decrease, reduction of overweight, and obesity including morbid obesity (e.g., by controlling appetite, ingestion, food intake, calorie intake, and/or energy consumption), but also for treating obesity-related inflammation, obesity-related gallbladder disease, and obesity-induced sleep apnea, but is not limited thereto, and may be used for treating the associated diseases or health conditions thereof.

The peptide of the present invention may also be used for treating metabolic syndrome other than obesity, i.e., obesity-related diseases such as impaired glucose tolerance, hypercholesterolemia, dyslipidemia, obesity, diabetes, hypertension, nonalcoholic steatohepatitis (nonalcoholic steatohepatitis, NASH), atherosclerosis caused by dyslipidemia, atherosclerosis, arteriosclerosis, coronary heart disease, stroke, hypoglycemia, etc. However, the effects of the peptide according to the present invention may be mediated entirely or partially by the body weight-related effects described above or may be independent of the same.

Examples of the compound or material having a therapeutic activity for metabolic syndrome to be included in the combined administration or the composition of the present invention may include an insulinotropic peptide, a glucagon like peptide-1 (GLP-1) receptor agonist, a leptin receptor agonist, a dipeptidyl peptidase-IV (DPP-IV) inhibitor, a Y5 receptor antagonist, a melanin-concentrating hormone (MCH) receptor antagonist, a Y2/4 receptor agonist, a melanocortin 3/4 (MC 3/4) receptor agonist, a gastric/pancreatic lipase inhibitor, an agonist of 5-hydroxytryptamine receptor 2C (5HT2C), a β3A receptor agonist, an amylin receptor agonist, a ghrelin antagonist, a ghrelin receptor antagonist, a peroxisome proliferator-activated receptor alpha (PPARα) agonist, a peroxisome proliferator-activated receptor delta (PPARδ) agonist, a Farnesoid X receptor (FXR) agonist, an acetyl-CoA carboxylase inhibitor, a peptide YY, cholecystokinin (CCK), xenin, glicentin, obestatin, secretin, nesfatin, insulin, and a glucose-dependent insulinotropic peptide (GIP), but is not limited thereto. Additionally, all medicaments which are effective for obesity treatment and the medicaments capable of inhibiting hepatic inflammation and fibrosis may be included.

Specifically, the insulinotropic peptide may be selected from the group consisting of GLP-1, exendin-3, exendin-4, an agonist thereof, a derivative thereof, a fragment thereof, a variant thereof, and a combination thereof.

More specifically, the insulinotropic peptide may be an insulinotropic peptide derivative in which the N-terminal histidine of the insulinotropic peptide is substituted with one selected from the group consisting of desamino-histidyl, N-dimethyl-histidyl, β-hydroxy imidazopropionyl, 4-imidazoacetyl, and β-carboxy imidazopropionyl, but is not limited thereto.

More specifically, the insulinotropic peptide may be selected from the group consisting of a native exendin-4; an exendin-4 derivative in which the N-terminal amine group of exendin-4 is deleted; an exendin-4 derivative in which the N-terminal amine group of exendin-4 is substituted with a hydroxyl group; an exendin-4 derivative in which the N-terminal amine group of exendin-4 is modified with a dimethyl group; an exendin-4 derivative in which the α-carbon of the $1^{St}$ amino acid of exendin-4, histidine, is deleted; an exendin-4 derivative in which the $12^{th}$ amino acid of exendin-4, lysine, is substituted with serine, and an exendin-4 derivative in which the $12^{th}$ amino acid of exendin-4, lysine, is substituted with arginine, but is not limited thereto.

Meanwhile, as an example of the insulinotropic peptide or a long-acting conjugate thereof, the entire disclosure of U.S. Patent Application Publication No. 2010-0105877 is enclosed in the present invention as a reference.

In a more specific embodiment, a glucagon derivative, for example, a peptide including the amino acid sequence of General Formula 1 or General Formula 2, may be in the form of a long-acting conjugate to which a biocompatible material capable of increasing in vivo half-life is linked, but is not limited thereto. The biocompatible material may be interchangeably used with a carrier.

Additionally, the insulinotropic peptide may also be in the form of a long-acting conjugate to which a biocompatible material capable of increasing in vivo half-life is linked, but is not limited thereto.

In a specific embodiment of the present invention, the duration of efficacy of the above conjugate increases compared to native glucagon or a glucagon derivative thereof, to which a carrier is not linked. In the present invention, the protein conjugate is called "a long-acting conjugate".

Examples of the biocompatible material may include polyethylene glycol, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, and a polymer, but are not limited thereto. For example, at least one amino acid side chain within the peptide of the present invention may be attached to the biocompatible material in order to increase in vivo solubility and/or half-life, and/or increase bioavailability thereof. These modifications are known to reduce the clearance of therapeutic proteins and peptides.

For the biocompatible polymer, soluble (amphipathic or hydrophilic), non-toxic, and pharmaceutically inert polymers are appropriate, and for example, they may include PEG, homopolymers or copolymers of PEG, monomethyl-substituted polymers (mPEG), and poly-amino acids such as poly-lysine, poly-aspartic acid, and poly-glutamic acid, but are not limited thereto.

It is a known fact to a skilled person in the art that the thus-modified glucagon derivative would have a superior therapeutic effect compared to native glucagon. Accordingly, the variants of the glucagon derivative as described above also belong to the scope of the present invention.

In a more specific embodiment, the glucagon derivative, for example, the peptide which includes the amino acid sequence of General Formula 1 or General Formula 2, and the insulinotropic peptide may be respectively linked to a biocompatible material by a linker selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, fatty acid, a polymer, a low molecular weight compound, a nucleotide, and a combination thereof, but is not limited thereto.

In an even more specific embodiment, the biocompatible material may be an FcRn-binding material, and the glucagon derivative, for example, the peptide which includes the amino acid sequence of General Formula 1 or General Formula 2, and the insulinotropic peptide may be respectively linked to a biocompatible material by a peptide linker or a non-peptide linker, but is not limited thereto.

As a specific example, the FcRn-binding material may be a polypeptide including an immunoglobulin Fc region.

As used herein, "non-peptide linker" includes a biocompatible polymer to which at least two repeating units are linked. The repeating units are linked with each other by a random covalent bond instead of a peptide bond. The non-peptide linker may be one constitution that establishes a moiety of a long-acting conjugate of the present invention.

As used herein, the term "non-peptide linker" may be used interchangeably with "non-peptide polymer".

Additionally, in a specific embodiment, the conjugate may be one in which the protein drug is covalently linked to the immunoglobulin Fc region by a non-peptide linker including a reactive group, which can be linked to the immunoglobulin Fc region and a protein drug on both ends of the conjugate.

Although not particularly limited, the non-peptide linker may be one selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, a polysaccharide, and a combination thereof. In a more specific embodiment, the non-peptide polymer may be polyethylene glycol, but is not limited thereto. Additionally, the derivatives which are already known in the art and the derivatives which can be easily prepared at the level of the technology in the art belong to the scope of the present invention.

The non-peptide linker to be used in the present invention may be any polymer which has a resistance to in vivo proteases, without limitation. The molecular weight of the non-peptide polymer may be in the range of 1 kDa to 100 kDa, and specifically, 1 kDa to 20 kDa, but is not limited thereto. Additionally, the non-peptide linker of the present invention, which is linked to the polypeptide including the immunoglobulin Fc region, may include not only a single kind of a polymer but also a combination of different kinds of polymers.

In a specific embodiment, both ends of the non-peptide linker may be respectively linked to an amine group or a thiol group of a peptide, which comprises the amino acid sequence of General Formula 1, or an insulinotropic peptide, and a biocompatible material.

Specifically, the non-peptide polymer may include a reactive group on both ends, respectively, which can be linked to an immunoglobulin Fc fragment and, a glucagon derivative or an insulinotropic peptide; and specifically, a reactive group which can be linked to an amine group of N-terminus or lysine, or a thiol group of cystenine of the glucagon derivative or the insulinotropic peptide, or the immunoglobulin Fc fragment.

Additionally, the reactive group of the non-peptide polymer that can be linked to the immunoglobulin Fc region, the glucagon derivative, and the insulinotropic peptide may be selected from the group consisting of an aldehyde group, a maleimide group, and a succinimide derivative, but is not limited thereto.

In the above, examples of the aldehyde group may include a propionaldehyde group or a butyraldehyde group, but are not limited thereto.

In the above, as a succinimide derivative, succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate may be used, but is not limited thereto.

Additionally, the final product produced through reductive alkylation via an aldehyde bond is more stable than that linked by an amide bond. The aldehyde reactive group selectively reacts with a N-terminus at a low pH condition while it can form a covalent bond with a lysine residue at high pH, e.g., pH 9.0.

The reactive groups at both ends of the non-peptide linker may be the same as or different from each other, for example, a maleimide reactive group may be provided at one end and an aldehyde group, a propionaldehyde group, or a butyraldehyde group may be provided at the other end. However, if an immunoglobulin Fc region and a glucagon derivative or an insulinotropic peptide can be conjugated at each end of the non-peptide linker, it is not particularly limited.

For example, the non-peptide polymer may possess a maleimide group at one end and an aldehyde group, a propionaldehyde group, or a butyraldehyde group at the other end.

When a polyethylene glycol having a reactive hydroxy group at both ends thereof is used as the non-peptide polymer, the hydroxy group may be activated to various reactive groups by known chemical reactions, or a polyethylene glycol having a commercially available modified reactive group may be used so as to prepare the long-acting protein conjugate of the present invention.

In a specific embodiment, the non-peptide polymer may be one which can be linked to a cysteine residue of a glucagon derivative, and more specifically, to the —SH group of cysteine, but is not limited thereto.

In a specific embodiment, the conjugate may be one in which a peptide including the amino acid sequence of SEQ ID NO: 12 or SEQ ID NO: 20 is linked to the immunoglobulin Fc region by a non-peptide polymer, and in particular, the non-peptide polymer may be one which is linked to the cysteine residue located on the 30$^{th}$ of the amino acid sequence of SEQ ID NO: 12 or the cysteine residue located on the 17$^{th}$ of the amino acid sequence of SEQ ID NO: 20, but is not limited thereto.

When maleimide-PEG-aldehyde is used, the maleimide group may be linked to the —SH group of the glucagon derivative by a thioether bond and the aldehyde group may be linked to the —NH$_2$ of the immunoglobulin Fc through reductive alkylation, but is not limited thereto and the above is merely an embodiment.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of a protein conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in a specific embodiment, the immunoglobulin Fc region may be in a dimeric form, and one molecule of a glucagon derivative or insulinotropic peptide may be covalently linked to a Fc region in a dimeric form, and in particular, the immunoglobulin Fc and the glucagon derivative or the insulinotropic peptide may be interlinked by a non-peptide polymer. Furthermore, two molecules of the glucagon derivative or insulinotropic peptide may be possibly conjugated in a symmetrical manner to a single Fc region in a dimeric form. In particular, the immunoglobulin Fc and the glucagon derivative or the insulinotropic peptide may be interlinked by a non-peptide linker, but are not limited to the embodiment described above.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be in the binding of an immunoglobulin Fc, may be used as suitable sites for modification.

Additionally, other various derivatives are possible, including one that has a deletion of a region capable of forming a disulfide bond, or a deletion of some amino acid residues at the N-terminus of native Fc or an addition of a methionine residue at the N-terminus of native Fc. Further, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions. In addition, the Fc region may, if necessary, be modified by phosphorylation, sulfation, acrylation, glycosylation, methylation, farnesylation, acetylation, amidation, etc.

The above-described Fc derivatives show biological activity identical to that of the Fc region of the present invention and have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinants or derivatives thereof, obtained from transformed animal cells or microorganisms. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size exclusion chromatography, etc. In a more specific embodiment, a human-derived Fc region is a recombinant immunoglobulin Fc region obtained from a microorganism.

In addition, the immunoglobulin Fc region may have natural glycans, increased or decreased glycans compared to the natural type, or be in a deglycosylated form. The increase, decrease, or removal of the glycans of the immunoglobulin Fc may be achieved by conventional methods such as a chemical method, an enzymatic method, and a genetic engineering method using a microorganism. The immunoglobulin Fc region obtained by removal of glycans from the Fc region shows a significant decrease in binding affinity to the C1q part and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier.

As used herein, the term "deglycosylation" refers to enzymatically removing sugar moieties from an Fc region, and the term "aglycosylation" refers to an unglycosylated Fc region produced in prokaryotes, more specifically, *E. coli.*

Meanwhile, the immunoglobulin Fc region may be derived from humans or other animals including cows, goats, pigs, mice, rabbits, hamsters, rats, and guinea pigs. In a more specific embodiment, it is derived from humans.

In addition, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The composition of the present invention can be used for preventing or treating hypoglycemia or metabolic syndromes.

As used herein, the term "prevention" refers to all kinds of actions associated with the inhibition or delay of the occurrence of hypoglycemia or metabolic syndrome by the administration of the peptide or the composition, and the term "treatment" refers to all kinds of actions associated with the improvement or advantageous changes in symptoms of hypoglycemia or metabolic syndrome by the administration of the peptide or the composition.

As used herein, the term "administration" refers to an introduction of a particular material to a patient by an appropriate manner. The composition may be administered by a general route that enables the delivery of the composition to a target tissue in vivo, for example, intraperitoneal, intravenous, intramuscular, subcutaneous, intradermal, oral, topical, intranasal, intrapulmonary, and intrarectal administration, but is not particularly limited thereto.

As used herein, the term "metabolic syndrome" refers to a symptom of a single or complex occurrence of various diseases due to chronic metabolic disorder, and in particular, examples of metabolic syndrome may include impaired glucose tolerance, hypercholesterolemia, dyslipidemia, obesity, diabetes, hypertension, nonalcoholic steatohepatitis (NASH), atherosclerosis caused by dyslipidemia, atherosclerosis, arteriosclerosis, coronary heart disease, stroke, etc., but are not limited thereto.

As used herein, the term "obesity" refers to a medical condition with excess body fat in the body, and a person having a body mass index (BMI; body mass (kg) divided by the square of the body height (m)) of 25 or higher is diagnosed as having obesity. Obesity generally occurs due to a long-term energy imbalance in which energy intake exceeds energy expenditure. Obesity is a metabolic disease that affects the entire body, which increases the risk of diabetes, hyperlipidemia, sexual dysfunction, arthritis, and cardiovascular disease, and in some cases, it is also associated with the occurrence of cancers.

Diabetes may represent "hypoglycemia" as an acute symptom.

As used herein, the term "hypoglycemia" refers to an acute symptom of diabetes, in which blood glucose levels are lower than those of normal people, and in general, refers to a state when the blood glucose levels are 50 mg/dL or less. Hypoglycemia is frequently caused when a person who takes an oral hypoglycemic agent or insulin has eaten less than usual or has performed activities or exercised more than usual. In addition, hypoglycemia may occur due to the use of glucose level-lowering drugs, severe physical diseases, deficiency in hormones such as adrenocortical hormones and glucagon, tumor in insulin-producing pancreas, autoimmune insulin syndrome, gastrectomy patients, hereditary carbohydrate metabolism disorder, etc.

Symptoms of hypoglycemia include weakness, trembling, pale skin, cold sweats, dizziness, excitement, anxiety, pounding heart, empty stomach, headache, fatigue, etc. In the case of persistent hypoglycemia, it may lead to convulsion or seizure, and may cause shock and thus fainting.

The pharmaceutical composition of the present invention may contain a pharmaceutically acceptable carrier, excipient, or diluent. As used herein, the term "pharmaceutically acceptable" refers to the properties of having a sufficient amount to exhibit a therapeutic effect and not causing adverse effects, and may be easily determined by a skilled person in the art based on the factors well known in the medical field, such as the kind of disease, age, body weight, health status, sex, drug sensitivity of a patient, administration route, administration method, administration frequency, duration of treatment, a drug to be mixed or administered simultaneously in combination, etc.

The pharmaceutical composition of the present invention containing the peptide of the present invention may further contain a pharmaceutically acceptable carrier. The pharmaceutically acceptable carrier may include, for oral administration, a binder, a glidant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc., although it is not limited thereto.

The formulation type of the composition according to the present invention may be prepared variously by combining with a pharmaceutically acceptable carrier as described above. For example, for oral administration, the composition may be formulated into tablets, troches, capsules, elixirs, suspensions, syrups, wafers, etc. For injections, the composition may be formulated into single-dose ampoules or multidose containers. The composition may be also formulated into solutions, suspensions, tablets, capsules, and sustained-release formulations.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the pharmaceutical composition of the present invention may be prepared in any formulation type selected from the group consisting of tablets, pills, powders, granules, capsules, suspensions, liquid medicine for internal use, emulsions, syrups, sterile injection solutions, non-aqueous solvents, lyophilized formulations, and suppositories.

Additionally, the composition may be formulated into a single dosage form suitable for the patient's body, and preferably is formulated into a preparation useful for peptide drugs according to the typical method used in the pharmaceutical field to be administered by an oral or parenteral route, such as through skin, intravenously, intramuscularly, intra-arterially, intramedullarily, intrathecally, intraventricularly, pulmonarily, transdermally, subcutaneously, intraperitoneally, intranasally, intragastrically, topically, sublingually, vaginally, or rectally, but is not limited thereto.

Additionally, the peptide may be used by blending with various pharmaceutically acceptable carriers such as physiological saline or organic solvents. In order to increase the stability or absorptivity, carbohydrates such as glucose, sucrose, or dextrans; antioxidants such as ascorbic acid or glutathione; chelating agents; low molecular weight proteins; or other stabilizers may be used.

The administration dose and frequency of the pharmaceutical composition of the present invention are determined by the type of active ingredient(s), along with various factors, such as the disease to be treated, administration route, patient's age, sex, and body weight, and severity of the disease.

The total effective dose of the composition of the present invention may be administered to a patient in a single dose, or may be administered for a long period of time in multiple doses according to a fractionated treatment protocol. In the pharmaceutical composition of the present invention, the content of active ingredient(s) may vary depending on the disease severity. Specifically, the preferable total daily dose of the peptide of the present invention may be approximately 0.0001 μg to 500 mg per 1 kg of body weight of a patient. However, the effective dose of the peptide is determined considering various factors including patient's age, body weight, health conditions, sex, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

The pharmaceutical composition of the present invention shows excellent in vivo duration of efficacy and titer, and thus the number and frequency of administration of the pharmaceutical preparation of the present invention can be significantly reduced.

In particular, since the pharmaceutical composition of the present invention contains, as an active ingredient, a glucagon derivative having an altered pI different from that of native glucagon, it shows improved solubility and high stability according to the pH of a given solution, and thus the pharmaceutical composition of the present invention can be effectively used in the preparation of a stable glucagon formulation for treating hypoglycemia or obesity.

In another aspect, the present invention provides a novel glucagon derivative.

The glucagon derivative is the same as explained above.

More specifically, the derivative is characterized in that it is an isolated peptide including the amino acid sequence of the following General Formula 2.

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine, or is absent,
with the proviso that when the amino acid sequence of General Formula 2 is identical to any one of SEQ ID NOS: 14, 19, 20, 25, 27, 31, and 33, it may be excluded.

More specifically, the amino acid pair of X16 and X20 of General Formula 2 may be one substituted with glutamic acid or lysine, respectively, which is capable of forming a ring, thereby forming a ring (e.g., a lactam ring) by the amino acid pair of X16 and X20, but is not limited thereto.

Additionally, the C-terminus of the peptide including the amino acid sequence of General Formula 2 may be amidated, but is not limited thereto.

Additionally, the peptide may be a glucagon derivative capable of activating a glucagon receptor, but is not limited thereto.

More specifically, the peptide may include an amino acid sequence selected from the group consisting of SEQ ID NOS: 12, 13, 15, and 36 to 44, but is not limited thereto.

In still another aspect, the present invention provides an isolated polynucleotide encoding the glucagon derivative, a vector including the polynucleotide, and an isolated cell including the polynucleotide or the vector.

The glucagon derivative is the same as explained above.

Additionally, the isolated polynucleotide encoding the glucagon derivative includes within the scope of the present invention a polynucleotide sequence having a homology of 75% or higher, specifically 85% or higher, more specifically 90% or higher, and even more specifically 95% or higher, to the corresponding sequence.

As used herein, the term "homology" indicates sequence similarity with a wild-type amino acid sequence or wild-type nucleotide sequence, and the homology comparison may be done with the naked eye or using a commercially available comparison program. Using a commercially available computer program, the homology between two or more sequences may be expressed as a percentage (%), and the homology (%) between adjacent sequences may be calculated.

*507As used herein, the term "recombinant vector" refers to a DNA construct including the sequence of a polynucleotide encoding a target peptide, e.g., a glucagon derivative, which is operably linked to an appropriate regulatory sequence to enable the expression of the target peptide, e.g., a glucagon derivative, in a host cell.

The regulatory sequence includes a promoter capable of initiating transcription, any operator sequence for the regulation of the transcription, a sequence encoding an appropriate mRNA ribosome-binding domain, and a sequence regulating the termination of transcription and translation. The recombinant vector, after being transformed into a suitable host cell, may be replicated or function irrespective of the host genome, or may be integrated into the host genome itself.

The recombinant vector used in the present invention may not be particularly limited as long as the vector is replicable in the host cell, and it may be constructed using any vector known in the art. Examples of the vector conventionally used may include natural or recombinant plasmids, cosmids, viruses, and bacteriophages. The vectors to be used in the present invention may be any expression vector known in the art.

The recombinant vector is used for the transformation of a host cell for producing glucagon derivatives of the present invention. Additionally, these transformed cells, as a part of the present invention, may be used for the amplification of nucleic acid fragments and vectors, or may be cultured cells or cell lines used in the recombinant production of glucagon derivatives of the present invention.

As used herein, the term "transformation" refers to a process of introducing a recombinant vector including a polynucleotide encoding a target protein into a host cell, thereby enabling the expression of the protein encoded by the polynucleotide in the host cell. For the transformed polynucleotide, it does not matter whether it is inserted into the chromosome of a host cell and located thereon or located outside of the chromosome, as long as it can be expressed in the host cell, and both cases are included.

Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette, which is a gene construct including all the essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell, but is not limited thereto.

Additionally, as used herein, the term "operably linked" refers to a functional connection between a promoter sequence, which initiates and mediates the transcription of the polynucleotide encoding the target peptide of the present invention, and the above gene sequence.

An appropriate host to be used in the present invention may not be particularly limited as long as it can express the polynucleotide of the present invention. Examples of the appropriate host may include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Pichia pastoris, Saccharomyces cerevisiae*, and *Schizosaccharomyces pombe*; insect cells such as *Spodoptera frugiperda* (Sf9), and animal cells such as CHO, COS, and BSC.

In still another aspect, the present invention provides an isolated conjugate in which a glucagon derivative and a biocompatible material which is capable of increasing in vivo half-life are linked. The conjugate may be a long-acting conjugate.

Regarding the glucagon derivative, the biocompatible material, and the constitution of the conjugate, all those described above are applied.

Specifically, the biocompatible material may be selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, saccharide, and a polymer, but is not limited thereto.

Additionally, the isolated peptide may be linked to a biocompatible material by a linker selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, fatty acid, a polymer, a low molecular weight compound, a nucleotide, and a combination thereof, but is not limited thereto.

Additionally, the biocompatible material may be an FcRn-binding material, and the isolated peptide may be linked to a biocompatible material by a peptide linker or a non-peptide linker selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, and a combination thereof, but is not limited thereto.

Additionally, the FcRn-binding material may be a polypeptide including the immunoglobulin Fc region, but is not limited thereto.

In still another aspect, the present invention provides a composition containing the glucagon derivative or the isolated conjugate.

The glucagon derivative and the isolated conjugate are the same as explained above.

Specifically, the composition may be a pharmaceutical composition for treating or preventing hypoglycemia or metabolic syndrome, but is not limited thereto. The pharmaceutical composition is the same as described above.

Additionally, the composition may be a composition containing the peptide of the amino acid sequence of the following General Formula 2.

(General Formula 2, SEQ ID NO: 46)
Y-Aib-QGTF-X7-SD-X10-S-X12-Y-L-X15-X16-X17-R-A-

X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine or is absent,
with the proviso that when the amino acid sequence of General Formula 2 is identical to any one of SEQ ID NOS: 14, 19, 20, 25, 27, 31, and 33, it may be excluded.

In still another aspect, the present invention provides a method for preventing or treating hypoglycemia or metabolic syndrome, including administering the above composition to a subject.

The composition, hypoglycemia, metabolic syndrome, prevention, and treatment are the same as explained above.

In the present invention, the term "subject" refers to those suspected of having hypoglycemia or metabolic syndrome, which means mammals including humans, mice, and livestock having hypoglycemia or metabolic syndrome or having the risk of hypoglycemia or metabolic syndrome. However, any subject to be treated with the glucagon derivative of the present invention or the composition containing the same is included without limitation. Further, the subject suspected of having hypoglycemia or obesity can be effectively treated by administering with the pharmaceutical composition containing the glucagon derivative of the present invention. The hypoglycemia and obesity are the same as explained above.

The method of the present invention may include administering the pharmaceutical composition containing the peptide at a pharmaceutically effective amount. The total daily dose should be determined within appropriate medical judgment by a physician, and administered once or several times in divided doses. Regarding the objects of the present invention, the specific therapeutically effective dose for any particular patient may be preferably applied differently, depending on various factors well known in the medical art, including the kind and degree of the response to be achieved, specific compositions including whether other agents are occasionally used therewith or not, the patient's age, body weight, general health conditions, sex and diet, the time and route of administration, secretion rate of the composition, duration of treatment, other drugs used in combination or concurrently with the composition of the present invention, and like factors well known in the medical arts.

In still another aspect, the present invention provides use of the glucagon derivative or the isolated conjugate or the composition in the preparation of a medicament (or a pharmaceutical composition) for preventing or treating hypoglycemia or metabolic syndrome.

The glucagon derivative, the isolated conjugate, the composition, hypoglycemia, and metabolic syndrome are the same as explained above.

MODE FOR INVENTION

Hereinafter, the present invention will be described in more detail with reference to the following examples and experimental examples. However, the following examples and experimental examples are provided for illustrative purposes only, and the scope of the present invention should not be limited thereto in any manner.

Example 1: Production of Cell Line Showing cAMP Response to Glucagon

PCR was performed using a region corresponding to Open Reading Frame (ORF) in the cDNA (OriGene Technologies, Inc., USA) of human glucagon receptor gene as a template along with the following forward and reverse primers (SEQ ID NOS: 47 and 48, respectively), which include each of the EcoRI and XhoI restriction sites.

In particular, PCR was performed for a total of 30 cycles under the following conditions: 95° C. denaturation for 60 sec, annealing at 55° C. for 60 sec, and polymerization at 68° C. for 30 sec. The amplified PCR products were subjected to a 1.0% agarose gel electrophoresis and a 450 bp band was obtained by elution.

```
Forward primer (SEQ ID NO: 47):
5'-CAGCGACACCGACCGTCCCCCCGTACTTAAGGCC-3'

Reverse primer (SEQ ID NO: 48):
5'-CTAACCGACTCTCGGGGAAGACTGAGCTCGCC-3'
```

The PCR product was cloned into a known animal cell expression vector, x0GC/dhfr, to prepare a recombinant vector x0GC/GCGR.

CHO DG44 cell line cultured in DMEM/F12 (10% FBS) medium was transfected with the recombinant vector x0GC/GCGR using Lipofectamine®, and cultured in a selection medium containing G418 (1 mg/mL) and methotraxate (10 nM). Single clone cell lines were selected therefrom by a limit dilution technique, and a cell line showing excellent cAMP response to glucagon in a concentration-dependent manner was finally selected therefrom.

Example 2: Synthesis of Glucagon Derivative

In order to prepare glucagon derivatives with improved physical properties, the amino acid sequence of native glucagon of SEQ ID NO: 1 was substituted with amino acid residues having positive and negative charges, and thereby glucagon derivatives were synthesized as shown in Table 1 below. The relative in vitro activities described below were measured by the method described in Example 4.

TABLE 1

Amino acid sequences of native glucagon and glucagon derivatives

| SEQ ID NO | Peptide Sequence | Ring Formation | pI | In vitro Activity (Relative Activity of SEQ ID NO: 1, %) |
|---|---|---|---|---|
| SEQ ID NO: 1 | HSQGTFTSDYSKYLDSRRAQDFVQWLMNT | — | 6.8 | 100 |
| SEQ ID NO: 2 | HSQGTFTSDYSKYLDCDRAQDFVQWLMNT | — | 4.56 | 0.6 |
| SEQ ID NO: 3 | HSQGTFTSDYSKYLDCERAQDFVQWLMNT | — | 4.66 | 6.1 |
| SEQ ID NO: 4 | HSQGTFTSDYSKYLDSCDAQDFVQWLMNT | — | 4.13 | <0.1 |

TABLE 1-continued

Amino acid sequences of native glucagon and glucagon derivatives

| SEQ ID NO | Peptide Sequence | Ring Formation | pI | In vitro Activity (Relative Activity of SEQ ID NO: 1, %) |
|---|---|---|---|---|
| SEQ ID NO: 5 | HSQGTFTSDYSKYLDSCEAQDFVQWLMNT | — | 4.22 | 0.3 |
| SEQ ID NO: 6 | HSQGTFTSDYSKYLDSCEADDFVQWLMNT | — | 4.03 | <0.1 |
| SEQ ID NO: 7 | YSQGTFTSDYSKYLDSCEADDFVQWLMNT | — | 3.71 | <0.1 |
| SEQ ID NO: 8 | YXQGTFTSDYSKYLDSCDAQDFVQWLINT | — | 3.77 | <0.1 |
| SEQ ID NO: 9 | YXQGTFTSDYSKYLDSCDAQDFVVWLINT | — | 3.77 | <0.1 |
| SEQ ID NO: 10 | YXQGTFTSDYSKYLDSCDADDFVVWLINT | — | 3.66 | <0.1 |
| SEQ ID NO: 11 | YXQGTFTSDYSKYLDEKCAKEFVQWLMNT | — | 4.78 | 4.6 |
| SEQ ID NO: 12 | YXQGTFTSDYSKYLDEKRAKEFVQWLMNTC | ring formed | 6.20 | 56.3 |
| SEQ ID NO: 13 | YXQGTFTSDYSCYLDSRRAQDFVQWLMNT | — | 4.43 | 5.2 |
| SEQ ID NO: 14 | YXQGTFTSDYSKYLDCKRAKEFVQWLMNT | — | 8.12 | 18.1 |
| SEQ ID NO: 15 | YXQGTFTSDYSKYLCEKRAQDFVVWLMNT | — | 6.11 | 1.1 |
| SEQ ID NO: 16 | YXQGTFTSDYSKYLDCRRAQVFVQWLMRT | — | 9.11 | 4.2 |
| SEQ ID NO: 17 | YXQGTFTSDYSKYLDCVRAQDFVQWLMRT | — | 6.03 | 23.2 |
| SEQ ID NO: 18 | YXQGTFTSDYSKYLDSRRACDFRLWLMNT | — | 8.15 | <0.1 |
| SEQ ID NO: 19 | YXQGTFTSDYSKYLCEKRAKEFVQWLMNT | ring formed | 8.12 | 12.1 |
| SEQ ID NO: 20 | YXQGTFTSDYSKYLDECRAKEFVQWLMNT | ring formed | 4.78 | 299.7 |
| SEQ ID NO: 21 | YXQGTFTSDYSKYLDEKCAKEFVQWLMNT | ring formed | 4.78 | 57.8 |
| SEQ ID NO: 22 | YXQGTFTSDYSKYLDEKRCKEFVQWLMNT | ring formed | 6.20 | 147.8 |
| SEQ ID NO: 23 | YXQGTFTSDYSKYCDEKRAKEFVQWLMNT | ring formed | 6.20 | 76.8 |
| SEQ ID NO: 24 | YXQGTFTSDYSKCLDEKRAKEFVQWLMNT | ring formed | 6.21 | 58.0 |
| SEQ ID NO: 25 | YXQGTFTSDYSKYLDEKRAKCFVQWLMNT | ring formed | 8.12 | 46.9 |
| SEQ ID NO: 26 | WXQGTFTSDYSKYLDECRAKDFVQWLMNT | ring formed | 4.68 | 1.0 |
| SEQ ID NO: 27 | YXQGTFVSDYSKYLDECRAKDFVQWLMNT | ring formed | 4.68 | 93.6 |
| SEQ ID NO: 28 | WXQGTFVSDYSKYLDECRAKDFVQWLMNT | ring formed | 4.68 | <0.1 |

TABLE 1-continued

Amino acid sequences of native glucagon and glucagon derivatives

| SEQ ID NO | Peptide Sequence | Ring Formation | pI | In vitro Activity (Relative Activity of SEQ ID NO: 1, %) |
|---|---|---|---|---|
| SEQ ID NO: 29 | YXQGTFTSDYSKCLD<u>ERRA</u><u>K</u>DFVQWLMNT | ring formed | 6.15 | 61.3 |
| SEQ ID NO: 30 | WXQGTFTSDYSKCLD<u>ERRA</u><u>K</u>DFVQWLMNT | ring formed | 4.44 | 0.3 |
| SEQ ID NO: 31 | YXQGTFTSDYSKYLDC<u>KRAK</u><u>EF</u>VQWLMNT | ring formed | 8.12 | 6.3 |
| SEQ ID NO: 32 | -SQGTFTSDYSKYLD<u>E</u>CRA<u>K</u>EFVQWLMNT | ring formed | 4.78 | 0.7 |
| SEQ ID NO: 33 | YXQGTFTSDYSKYLDSRRAQDFVQWLMNT | – | 6.04 | 108.2 |
| SEQ ID NO: 34 | WXQGTFTSDYSKYCD<u>ERRA</u><u>K</u>EFVQWLMNT | ring formed | 6.21 | 0.2 |
| SEQ ID NO: 35 | YXQGTFTSDYSKYCD<u>ERRA</u><u>K</u>EFVQWLMNT | ring formed | 6.2 | 17.7 |
| SEQ ID NO: 36 | YXQGTFTSDCSKYLD<u>ERRA</u><u>K</u>EFVQWLMNT | ring formed | 6.21 | 9.9 |
| SEQ ID NO: 37 | YXQGTFTSDYSKYLD<u>ERRA</u><u>K</u>EFVQWLMNTC | ring formed | 6.21 | 225.5 |
| SEQ ID NO: 38 | YXQGTFCSDYSKYLD<u>ERRA</u><u>K</u>EFVQWLMNT | ring formed | 6.15 | 167.3 |
| SEQ ID NO: 39 | YXQGTFVSDCSKYLD<u>ERRA</u><u>K</u>DFVQWLMNT | ring formed | 6.15 | 3.7 |
| SEQ ID NO: 40 | YXQGTFVSDYSKYLD<u>ERRA</u><u>K</u>DFVQWLMNTC | ring formed | 6.15 | 40.8 |
| SEQ ID NO: 41 | YXQGTFCSDYSKYLD<u>ERRA</u><u>K</u>DFVQWLMNT | ring formed | 6.03 | 45.2 |
| SEQ ID NO: 42 | YXQGTFCSDYSKYLDSRRAQDFVQWLMNT | – | 6.03 | 37.9 |
| SEQ ID NO: 43 | YXQGTFTSDCSKYLDSRRAQDFVQWLMNT | – | 6.03 | 1.6 |
| SEQ ID NO: 44 | YXQGTFTSDYSKYLDSRRAQDFVQWLMNTC | – | 6.21 | 75.4 |

In the amino acids sequences described in Table 1, the amino acid represented by X represents a non-native amino acid, aminoisobutyric acid(Aib), the underlined amino acid residues represent formation of a ring, and "-" in the amino acid sequence indicates that no amino acid residue is present on the corresponding position.

Example 3: Measurement of pI of Glucagon Derivatives

In order to measure the improved physical properties of glucagon derivatives synthesized in Example 2, pI values were calculated based on the amino acid sequences using the pI/Mw tool (e.g., expasy.org/tools/pi_tool.html; Gasteiger et al., 2003) in the ExPASy server.

As shown in Table 1 above, while the native glucagon of SEQ ID NO: 1 had a pI of 6.8, the some glucagon derivatives according to the present invention showed pI values in the range of from about 4 to about 6. Since the glucagon derivatives according to the present invention have pI values lower or more than that of native glucagon, they can exhibit improved solubility and higher stability at a neutral pH condition compared to native glucagon.

Accordingly, when the glucagon derivatives according to the present invention are used as a therapeutic agent for treating hypoglycemia, they can improve patient compliance, and are also suitable for administration in combination with other anti-obesity agents or anti-diabetes agents, and thus the glucagon derivatives of the present invention can be effectively used as a therapeutic agent for treating hypoglycemia and metabolic syndromes including obesity, diabetes, nonalcoholic steatohepatitis (NASH), dyslipidemia, and coronary heart disease.

Example 4: Measurement of cAMP Activity of Glucagon Derivatives

The activities of the glucagon derivatives synthesized in Example 2 were measured in cell lines having the human glucagon receptors produced in Example 1. Specifically, the transfected cell line was subcultured 3 to 4 times a week, aliquoted into a 384-well plate in an amount of 6×10³ cell lines/well, and cultured for 24 hours. Native glucagon and glucagon derivatives were suspended in Hank's balanced salt solution (HBSS) buffer containing 0.5 mM of 3-isobutyl-1-methylxanthine (IBMX), 0.1% bovine serum albumin (BSA), and 5 mM 4-(2-hydroxyethyl)-1-piperazineethanesulfonic acid (HEPES) with the culture cells, at concentrations of 200 nM and 1600 nM, respectively, continuously subjected into a 4-fold dilution 10 times, applied to a cAMP assay kit (LANCE cAMP 384 kit, PerkinElmer), and added to the cultured cells, and their fluorescence value was measured. Upon measurement, the highest fluorescence value was set at 100% and then $EC_{50}$ values of the glucagon derivative were calculated based on the same and compared with that of native glucagon, respectively. The results are shown in Table 1 above.

Example 5: Preparation of a Conjugate Including a Glucagon Derivative and an Immunoglobulin Fc (SEQ ID NO: 12 or 20-Immunoglobulin Fc Region Conjugate)

For the pegylation of a 10 kDa PEG having a maleimide group and an aldehyde group, respectively, at both ends (named as "maleimide-PEG-aldehyde", 10 kDa, NOF, Japan) into the cysteine residue of a glucagon derivative (SEQ ID NOS: 12 and 20), the glucagon derivatives and maleimide-PEG-aldehyde were reacted at a molar ratio of 1:1 to 5, at a protein concentration of 3 mg/mL to 10 mg/mL at low temperature for 1 to 3 hours. In particular, the reaction was conducted in an environment in which 20% to 60% isopropanol was added. Upon completion of the reaction, the reactants were applied to SP sepharose HP (GE healthcare, USA) to purify the glucagon derivatives mono-pegylated on cysteine.

Then, the purified mono-pegylated glucagon derivatives and an immunoglobulin Fc were reacted at a molar ratio of 1:2 to 10, at a protein concentration of 10 mg/mL to 50 mg/mL at 4° C. to 8° C. for 12 hours to 18 hours. The reaction was conducted in an environment in which sodium cyanoborohydride ($NaCNBH_3$) and 10% to 20% isopropanol were added to 100 mM calcium phosphate buffer (pH 6.0). Upon completion of the reaction, the reactants were applied to the Butyl sepharose FF purification column (GE healthcare, USA) and Source ISO purification column (GE healthcare, USA) to purify the conjugate including the glucagon derivatives and the immunoglobulin Fc.

After preparation, the purity analyzed by reverse phase chromatography, size exclusion chromatography, and ion exchange chromatography was shown to be 95% or higher.

In particular, the conjugate in which the glucagon derivative of SEQ ID NO: 12 and an immunoglobulin Fc were linked by PEG was named as "the conjugate including the glucagon derivative of SEQ ID NO: 12 and an immunoglobulin Fc" or "a long-acting derivative of SEQ ID NO: 12", and they can be interchangeably used in the present invention.

In particular, the conjugate in which the glucagon derivative of SEQ ID NO: 20 and an immunoglobulin Fc were linked by PEG was named as "a conjugate including the glucagon derivative of SEQ ID NO: 20 and an immunoglobulin Fc" or "a long-acting derivative of SEQ ID NO: 20", and they can be interchangeably used in the present invention.

Example 6: Preparation of a Conjugate Including an Exendin-4 Derivative and an Immunoglobulin Fc A 3.4 kDa PEG having a propionaldehyde group at both ends, i.e., 3.4 k PropionALD (2) PEG, was reacted with the Lys of CA exendin-4 using imidazo-acetyl exendin-4 where the alpha carbon of N-terminal histidine was deleted (CA exendin-4, AP, USA), and then a coupling was conducted based on the isomer peak at the rearmost part (Lys27) between the two Lys peaks, which is quite reactive and clearly distinguished from the N-terminal isomer.

A peptide and an immunoglobulin Fc were reacted at a molar ratio of 1:8, at the total protein concentration of 60 mg/mL at 4° C. for 20 hours. The reactant was 100 mM K-P (pH 6.0) and 20 mM SCB, a reducing agent, was added. The coupling reactants were purified by passing through with two purification columns. First, a large amount of immunoglobulin Fc not involved in the coupling reaction was removed using the SOURCE Q (XK-16 mL, Amersham Biosciences). Upon application of a salt gradient using 1 M NaCl at 20 mM Tris (pH 7.5) results in the immediate elution of the immunoglobulin Fc, which has a relatively weak binding affinity, followed immediately by the elution of exendin-4-immunoglobulin Fc. The immunoglobulin Fc is removed to some extent by the primary purification, however, complete separation was not achieved by ion exchange column because of the small difference in binding affinity between the immunoglobulin Fc and the exendin-4-immunoglobulin Fc. Accordingly, secondary purification was performed using the hydrophobicity of the two different materials. The sample, which passed through the primary purification, was bound to the SOURCE ISO (HR16 mL, Amersham Biosciences) using 20 mM Tris (pH 7.5) and 1.5 M ammonium sulfate, and was then eluted while the concentration of ammonium sulfate was gradually lowered. As a result, the immunoglobulin Fc, which has a weak binding affinity for the HIC column, was eluted first, followed by the elution of the exendin-4-immunoglobulin Fc sample, which has a strong binding affinity, to the rear part. The separation was more easily performed compared with the ion exchange column due to the larger difference in hydrophobicity.

Column: SOURCE Q (XK 16 mL, Amersham Biosciences)
Flow rate: 2.0 mL/min
Gradient: A0→25% 70 min B (A: 20 mM Tris, pH 7.5, B: A+1 M NaCl)
Column: SOURCE ISO (HR 16 mL, Amersham Biosciences)
Flow rate: 7.0 mL/min
Gradient: B 100→0% 60 min B [A: 20 mM Tris (pH 7.5), B: A+1.5 M ammonium sulfate (($NH_4)_2SO_4$)]

The thus-prepared conjugate, in which the exendin-4 derivative and the immunoglobulin Fc region were linked by PEG, was named as "a long-acting exendin-4 derivative". Also, such term can be interchangeable used with "a long-acting exendin derivative" in the present invention.

Experimental Example 1

Effect of Body Weight Reduction in Rats with High Fat Diet-Induced Obesity

In this experiment, high-fat diet-induced obesity rats, which are widely used as obesity animal models, were used. The body weight of the rats before administration was about 600 g. The rats were housed individually during the experiment and were given ad libitum access to water. Lighting was not provided between 6 AM and 6 PM.

The test groups fed with high-fat diet include: Group 1, with an excipient (injection once every 3 days)-control group; Group 2, the long-acting exendin derivative of Example 6 at 3.3 nmol/kg (injection once every 3 days); Group 3, the long-acting derivative of SEQ ID NO: 12 at 1.6 nmol/kg (injection once every 3 days); Group 4, the long-acting derivative of SEQ ID NO: 12 at 3.3 nmol/kg (injection once every 3 days); Group 5, the long-acting derivative of SEQ ID NO: 12 at 6.6 nmol/kg (injection once every 3 days); Group 6, the long-acting exendin derivative of Example 6 at 3.3 nmol/kg+the long-acting derivative of SEQ ID NO: 12 at 1.6 nmol/kg (injection once every 3 days, respectively); Group 7, the long-acting exendin derivative of Example 6 at 3.3 nmol/kg+the long-acting derivative of SEQ ID NO: 12 at 3.3 nmol/kg (injection once every 3 days, respectively); Group 8, the long-acting exendin derivative of Example 6 at 3.3 nmol/kg+the long-acting derivative of SEQ ID NO: 12 at 6.6 nmol/kg (injection once every 3 days, respectively); Group 9, a paired-feeding with Group 4; and Group 10, a paired-feeding with Group 7. The experiment was terminated on the $15^{th}$ day, and the changes in body weight of the rats in each group were measured at 3-day intervals during the progress of the experiment. Upon termination of the experiment, the amount of mesenteric fat and liver weight were measured by autopsy. Statistical analysis was performed to compare between the excipient group (control group) and test groups by 1-way ANOVA.

As a result of the measurement of changes in body weight, as can be confirmed in FIG. 1, the groups administered with either the long-acting exendin derivative or the long-acting derivative of SEQ ID NO: 12 alone showed a decrease in body weight by −8% and −7% to −22%, compared to that before administration, whereas in groups with a combined administration of the long-acting exendin derivative and the long-acting derivative of SEQ ID NO: 12, the effect of reducing body weight was improved further from −22% to −35%.

Additionally, when the effect of a body weight decrease in the group administered with the long-acting derivative of SEQ ID NO: 12 alone and the group administered with the combination of the long-acting exendin derivative and the long-acting derivative of SEQ ID NO: 12 was compared with that of the paired feeding group, respectively, a difference of about −11% and about −17% was shown, respectively, thus confirming that the body weight reducing effect was shown when administered with the glucagon derivative alone or the combined administration, by actions other than dietary intake.

That is, it was confirmed that the long-acting glucagon derivative of the present invention could play an additional role in body weight reduction in addition to the effect of anorexia.

Additionally, as a result of the measurement of the amount of mesenteric fat and liver weight, as can be confirmed in FIGS. 2 and 3, the combined administration of the long-acting exendin derivative and the long-acting derivative of SEQ ID NO: 12 showed a significant decrease in body fat and also a decrease in the weight of the liver compared to that of the group administered with an excipient. In particular, the increase/decrease of the weight of the liver is generally caused by the increase/decrease of the fat present in the liver, and the above effect of decrease in the weight of the liver shows the effect of reducing the liver fat. Accordingly, the decrease of the fat in the liver can be measured as a method for measuring the therapeutic effect of metabolic syndrome such as obesity, diabetes, nonalcoholic steatohepatitis, etc.

Experimental Example 2

Effect of Body Weight Reduction in Mice with High Fat Diet-Induced Obesity

In this experiment, high-fat diet-induced obesity mice, which are widely used as obesity animal models, were used. The body weight of the mice before administration was about 55 g. The mice were housed 7 mice per each group during the experiment and were given ad libitum access to water. Lighting was not provided between 6 AM and 6 PM.

The test groups fed with high-fat diet include: Group 1, with an excipient (injection once every 2 days)-control group; Group 2, the long-acting exendin derivative of Example 6 at 4.3 nmol/kg (injection once every 2 days); Group 3, the long-acting derivative of SEQ ID NO: 20 at 4.4 nmol/kg (injection once every 2 days); Group 4, the long-acting derivative of SEQ ID NO: 20 at 8.8 nmol/kg (injection once every 2 days); Group 5, the long-acting exendin derivative of Example 6 at 4.3 nmol/kg+the long-acting derivative of SEQ ID NO: 20 at 4.4 nmol/kg (injection once every 2 days); Group 6, the long-acting exendin derivative of Example 6 at 2.1 nmol/kg+the long-acting derivative of SEQ ID NO: 20 at 6.6 nmol/kg (injection once every 2 days); and Group 7, the long-acting exendin derivative of Example 6 at 0.8 nmol/kg+the long-acting derivative of SEQ ID NO: 20 at 8.0 nmol/kg (injection once every 2 days). The experiment was terminated on the $22^{nd}$ day, and the changes in body weight of the mice in each group were measured at 2-day intervals during the progress of the experiment. Upon termination of the experiment, the weight of the mouse livers was measured by autopsy.

As a result of the measurement of changes in body weight, as can be confirmed in FIG. 4, each of the groups administered with the long-acting derivative of SEQ ID NO: 20 (8.8 nmol/kg, injection once every 2 days) alone showed a decrease in body weight by −25% and −29%, respectively, compared to that before administration. Additionally, the effect of reducing body weight was shown to increase further when administered in combination with the long-acting exendin derivative. It was also confirmed that the combined administration of the long-acting exendin derivative and the long-acting derivative of SEQ ID NO: 20 at a ratio of 1:1, 1:3, and 1:10 further increased the effect of reducing body weight by −50% or higher. Additionally, the effect of reducing body weight according to the ratio between the long-acting exendin derivative and the long-acting derivative of SEQ ID NO: 20 was not significant, however, the effect of anorexia became higher along with the increase in the percentage of the long-acting exendin derivative, thus confirming that the glucagon long-acting derivative of the present invention could play an additional role in body weight reduction in addition to the effect of anorexia.

Additionally, as a result of the measurement of the total cholesterol in the blood, as can be confirmed in FIG. 5, each of the groups administered with the long-acting exendin derivative (4.4 nmol/kg, injection once every 2 days) and the long-acting derivative of SEQ ID NO: 20 (8.8 nmol/kg, injection once every 2 days) showed a decrease in cholesterol by −35% and −71%, respectively. From the above, it was confirmed that the glucagon long-acting derivative of the present invention could play an additional role in reducing blood cholesterol in addition to the effect of anorexia. Statistical analysis was performed to compare between the excipient group (control group) and test groups by 1-way ANOVA.

Those of ordinary skill in the art will recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. An isolated peptide comprising the amino acid sequence of the following General Formula 2:

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30 wherein,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine or is absent,
with the proviso that a peptide of the amino acid sequence of SEQ ID NO: 12 is excluded.

2. The peptide of claim 1, wherein, the amino acid pair of X16 and X20 is respectively glutamic acid and lysine, which is capable of forming a ring.

3. The peptide of claim 1, wherein the C-terminus of the peptide is amidated.

4. The peptide of claim 1, wherein the peptide is a glucagon derivative capable of activating a glucagon receptor.

5. The peptide of claim 1, wherein the peptide comprises the amino acid sequence selected from the group consisting of SEQ ID NOS: 13, 15, 19, 33, and 36 to 44.

6. An isolated conjugate, wherein the isolated peptide of claim 1 and a biocompatible material capable of increasing in vivo half-life are linked.

7. The isolated conjugate of claim 6, wherein the biocompatible material is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, and a polysaccharide.

8. The isolated conjugate of claim 6, wherein the peptide is linked to a biocompatible material by a linker selected from the group consisting of polyethylene glycol, polypropylene glycol, an ethylene glycol-propylene glycol copolymer, polyoxyethylated polyol, polyvinyl alcohol, a polysaccharide, polyvinyl ethyl ether, polylactic acid (PLA), polylactic-glycolic acid (PLGA), lipid polymer, chitin, hyaluronic acid, fatty acid, a nucleotide, and a combination thereof.

9. The isolated conjugate of claim 6,
wherein the biocompatible material is an FcRn-binding material, and
the isolated peptide is linked to a biocompatible material by a peptide linker or a non-peptide linker selected from the group consisting of polyethylene glycol, polypropylene glycol, an ethylene glycol-propylene glycol copolymer, polyoxyethylated polyol, polyvinyl alcohol, a polysaccharide, polyvinyl ethyl ether, a polylactic acid (PLA), polylactic-glycolic acid (PLGA), lipid polymer, chitin, hyaluronic acid, and a combination thereof.

10. The isolated conjugate of claim 9, wherein the FcRn-binding material is a polypeptide comprising an immunoglobulin Fc region.

11. A composition comprising (i) the isolated peptide of claim 1 or (ii) an isolated conjugate in which the isolated peptide of claim 1 is linked to a biocompatible material capable of increasing in vivo half-life.

12. The composition of claim 11, which is a pharmaceutical composition comprising a pharmaceutically acceptable carrier.

13. A method for treating metabolic syndrome, comprising administering
(i) the isolated peptide of claim 1 or
(ii) an isolated conjugate in which the isolated peptide of claim 1 is linked to a biocompatible material capable of increasing in vivo half-life,
to a subject in need thereof,
wherein the metabolic syndrome is selected from the group consisting of hypercholesterolemia, obesity and nonalcoholic steatohepatitis.

14. The method of claim 13, wherein (i) the peptide or (ii) the conjugate comprises the amino acid sequence selected from the group consisting of SEQ ID NOS: 13, 15, 19, 33, and 36 to 44.

15. A pharmaceutical composition comprising
(i-a) the isolated peptide of claim 1 or (i-b) an isolated conjugate in which the isolated peptide of claim 1 is linked to a biocompatible material capable of increasing in vivo half-life; and
(ii) at least one compound or material having a therapeutic activity for metabolic syndrome.

16. The pharmaceutical composition of claim 15, wherein the isolated peptide comprises the amino acid sequence selected from the group consisting of SEQ ID NOS: 13, 15, 19, 33, and 36 to 44.

17. The pharmaceutical composition of claim 15, wherein (ii) the compound or material having a therapeutic activity for metabolic syndrome is selected from the group consisting of an insulinotropic peptide, a glucagon-like peptide-1 (GLP-1) receptor agonist, a leptin receptor agonist, a dipeptidyl peptidase-IV (DPP-IV) inhibitor, a Y5 receptor antagonist, a melanin-concentrating hormone (MCH) receptor antagonist, a Y2/4 receptor agonist, a melanocortin 3/4 (MC 3/4) receptor agonist, a gastric/pancreatic lipase inhibitor, an agonist of 5-hydroxytryptamine receptor 2C (5HT2C), a β3A receptor agonist, an amylin receptor agonist, a ghrelin antagonist, a ghrelin receptor antagonist, a peroxisome proliferator-activated receptor alpha (PPARα) agonist, a peroxisome proliferator-activated receptor delta (PPARδ) agonist, a Farnesoid X receptor (FXR) agonist, an acetyl-CoA carboxylase inhibitor, a peptide YY, cholecystokinin (CCK), xenin, glicentin, obestatin, secretin, nesfatin, insulin, and a glucose-dependent insulinotropic peptide (GIP).

18. The pharmaceutical composition of claim 17, wherein the insulinotropic peptide is selected from the group consisting of GLP-1, exendin-3, exendin-4, an agonist thereof, a derivative thereof, a fragment thereof, a variant thereof, and a combination thereof.

19. The pharmaceutical composition of claim 18, wherein the insulinotropic peptide is an insulinotropic peptide derivative, in which the N-terminal histidine residue is substituted with one selected from the group consisting of desamino-histidyl, N-dimethyl-histidyl, β-hydroxy imidazopropionyl, 4-imidazoacetyl, and β-carboxy imidazopropionyl.

20. The pharmaceutical composition of claim 18, wherein the insulinotropic peptide is selected from the group consisting of a native exendin-4; an exendin-4 derivative in which the N-terminal amine group of exendin-4 is deleted; an exendin-4 derivative in which the N-terminal amine group of exendin-4 is substituted with a hydroxyl group; an exendin-4 derivative in which the N-terminal amine group of exendin-4 is modified with a dimethyl group; an exendin-4 derivative in which the α-carbon of the $1^{st}$ amino acid of exendin-4, histidine, is deleted; an exendin-4 derivative in which the $12^{th}$ amino acid of exendin-4, lysine, is substituted with serine, and an exendin-4 derivative in which the $12^{th}$ amino acid of exendin-4, lysine, is substituted with arginine.

21. The method of claim 13, further comprising administering a compound or material having a therapeutic activity for metabolic syndrome, said administering being either before or after the administration of (i) the isolated peptide or (ii) the conjugate.

22. A method for treating hypoglycemia, comprising administering
(i) the isolated peptide of claim 1 or
(ii) an isolated conjugate in which the isolated peptide of claim 1 is linked to a biocompatible material capable of increasing in vivo half-life,
to a subject in need thereof.

23. The method of claim 22, further comprising administering a compound or material having a therapeutic activity for hypoglycemia, said administering being either before or after the administration of the isolated peptide or conjugate.

24. The method of claim 22, wherein (i) the peptide or (ii) the conjugate comprises the amino acid sequence selected from the group consisting of SEQ ID NOS: 13, 15, 19, 33, and 36 to 44.

25. The composition of claim 11, which is administered in combination with at least one compound or material having a therapeutic activity for metabolic syndrome or hypoglycemia.

26. A method for treating metabolic syndrome comprising administering in any sequential order
(i) a peptide comprising the isolated peptide of claim 1 or an isolated conjugate in which the isolated peptide of claim 1 is linked to a biocompatible material capable of increasing in vivo half-life; and
(ii) at least one compound or material having a therapeutic activity for metabolic syndrome,
wherein the metabolic syndrome is selected from the group consisting of hypercholesterolemia, obesity and nonalcoholic steatohepatitis.

27. The method of claim 26, wherein (i) the peptide or conjugate comprises the amino acid sequence selected from the group consisting of SEQ ID NOS: 13, 15, 19, 33, and 36 to 44.

* * * * *